United States Patent
Barker et al.

(10) Patent No.: US 10,342,772 B2
(45) Date of Patent: *Jul. 9, 2019

(54) PROCESSES FOR OBTAINING MICROBIAL OIL FROM MICROBIAL CELLS

(71) Applicant: DSM IP ASSETS B.V., TE Heerlen (NL)

(72) Inventors: Mark Barker, Mount Sterling, KY (US); Nasrin Tabayehnejad, Lexington, KY (US); Ginger Shank, Winchester, KY (US); Neil Leininger, Winchester, KY (US); Kirt Lyvell Matthews, Sr., Fort Mill, SC (US)

(73) Assignee: DSM IP Assets B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/106,365

(22) PCT Filed: Dec. 19, 2014

(86) PCT No.: PCT/US2014/071459
§ 371 (c)(1),
(2) Date: Jun. 20, 2016

(87) PCT Pub. No.: WO2015/095688
PCT Pub. Date: Jun. 25, 2015

(65) Prior Publication Data
US 2016/0317485 A1    Nov. 3, 2016

Related U.S. Application Data

(60) Provisional application No. 61/918,922, filed on Dec. 20, 2013.

(51) Int. Cl.
| | | |
|---|---|---|
| *A61K 31/202* | (2006.01) | |
| *C11B 1/02* | (2006.01) | |
| *C11B 1/10* | (2006.01) | |
| *C11B 3/04* | (2006.01) | |
| *A23L 33/115* | (2016.01) | |

(52) U.S. Cl.
CPC .......... *A61K 31/202* (2013.01); *A23L 33/115* (2016.08); *C11B 1/025* (2013.01); *C11B 1/108* (2013.01); *C11B 3/04* (2013.01)

(58) Field of Classification Search
CPC ....... C07C 57/03; C07C 51/42; C07C 51/487; C07C 51/48; C07C 57/02; C11B 1/025; C11B 1/10; C11B 1/02; C11B 3/00; C11B 3/001; C11B 3/02; C11B 3/06; C11B 3/16; C11B 1/108; C11B 3/04; C11B 1/14; C12P 7/6472; C12P 7/6463; C12P 7/6427; Y02E 50/16; A23D 9/00; A23L 33/115; A61K 31/202; C12N 1/066; C12N 15/52; C12N 9/0051; C12Q 1/6869; C12Q 2563/143; C12Q 2563/155; C12Q 2565/629; C12Q 1/6834; B01L 2200/0668; B01L 2200/0673; B01L 2300/0816; B01L 2300/1827; B01L 2300/1861; B01L 2400/043; B01L 2400/0487; B01L 3/502761; B01L 3/502784; B01L 7/52; A23K 10/12; A23K 20/158; B01D 21/265; B01F 11/025; B01F 2005/0637; B01F 5/0057; B01F 5/0074; B01F 5/0615; B01J 19/2405; B01J 19/241; B01J 2219/00772; C01B 15/027; C01B 3/02; C01B 3/06; C02F 11/00; C02F 1/36; C02F 1/38; C02F 1/40; C02F 1/441; C02F 1/4604; C02F 2101/30; C02F 2101/32; C02F 2103/08; C02F 2301/024; C02F 2301/026; C10G 31/10; C10G 32/00
See application file for complete search history.

(56) References Cited

U.S. PATENT DOCUMENTS

| | | |
|---|---|---|
| 2,753,362 A | 7/1956 | Owades et al. |
| 3,089,821 A | 5/1963 | Folkers |
| 3,878,232 A | 4/1975 | Hayes et al. |
| 4,504,473 A | 3/1985 | Cantrell |
| 4,680,314 A | 7/1987 | Nonomura |
| 4,720,456 A | 1/1988 | Wagner et al. |
| 4,792,418 A | 12/1988 | Rubin et al. |
| 4,857,329 A | 8/1989 | Sako et al. |
| 4,906,746 A | 3/1990 | Barnier et al. |
| 5,010,004 A | 4/1991 | Kosugi et al. |
| 5,130,242 A | 7/1992 | Barclay |
| 5,133,963 A | 7/1992 | Ise |

(Continued)

FOREIGN PATENT DOCUMENTS

| | | |
|---|---|---|
| CA | 2076018 C | 8/1991 |
| CA | 2146235 C | 4/1994 |

(Continued)

OTHER PUBLICATIONS

Akoh et al., Food Lipids, Chemistry Nutrition and Biotechnology, 1998, 208-385.

(Continued)

*Primary Examiner* — Deborah K Ware
(74) *Attorney, Agent, or Firm* — Shannon McGarrah; Xi Chen

(57) ABSTRACT

Processes are disclosed for obtaining a lipid from a cell by lysing the cell to form a lysed cell composition, adding an acid to lower the pH of the lysed cell composition, and demulsify the lysed cell composition, and obtaining the lipid from the demulsified lysed cell composition. Also disclosed are lipids prepared by the processes of the present invention wherein the lipids have a particular anisidine value, peroxide value, and/or phosphorus content.

40 Claims, No Drawings

(56) References Cited

U.S. PATENT DOCUMENTS

| | | |
|---|---|---|
| 5,173,409 A | 12/1992 | English |
| 5,179,012 A | 1/1993 | Gudin et al. |
| 5,288,619 A | 2/1994 | Brown et al. |
| 5,338,673 A | 8/1994 | Thepenier et al. |
| 5,340,594 A | 8/1994 | Barclay |
| 5,340,742 A | 8/1994 | Barclay |
| 5,397,591 A | 3/1995 | Kyle et al. |
| 5,476,787 A | 12/1995 | Yokoyama et al. |
| 5,492,938 A | 2/1996 | Kyle et al. |
| 5,539,133 A | 7/1996 | Kohn et al. |
| 5,583,019 A | 12/1996 | Barclay |
| 5,897,994 A | 4/1999 | Sandoz et al. |
| 5,928,696 A | 7/1999 | Best et al. |
| 5,951,875 A | 9/1999 | Kanel et al. |
| 5,969,169 A | 10/1999 | Fan |
| 6,127,185 A | 10/2000 | Melton et al. |
| 6,166,231 A | 12/2000 | Hoeksema |
| 6,180,376 B1 | 1/2001 | Liddell |
| 6,201,145 B1 | 3/2001 | Fan |
| 6,204,401 B1 | 3/2001 | Perrut et al. |
| 6,255,505 B1 | 7/2001 | Bijl et al. |
| 6,270,828 B1 | 8/2001 | DeBonte et al. |
| 6,344,349 B1 | 2/2002 | Moldavsky et al. |
| 6,447,782 B1 | 9/2002 | Viron et al. |
| 6,451,567 B1 | 9/2002 | Barclay |
| 6,509,178 B1 | 1/2003 | Tanaka et al. |
| 6,528,941 B1 | 3/2003 | Inubushi et al. |
| 6,541,049 B2 | 4/2003 | Barclay |
| 6,582,941 B1 | 6/2003 | Yokochi et al. |
| 6,607,900 B2 | 8/2003 | Bailey et al. |
| 6,750,048 B2 | 6/2004 | Ruecker et al. |
| 6,812,001 B2 | 11/2004 | Sibeijn et al. |
| 6,905,861 B2 | 6/2005 | Mitsuhashi et al. |
| 6,958,229 B2 | 10/2005 | Suzuki et al. |
| 7,163,811 B2 | 1/2007 | Behrens et al. |
| 7,351,558 B2 | 4/2008 | Ruecker et al. |
| 7,431,952 B2 | 10/2008 | Bijl et al. |
| 7,527,734 B1 | 5/2009 | Shepherd |
| 7,662,598 B2 | 2/2010 | Ruecker et al. |
| 7,781,193 B2 | 8/2010 | Ruecker et al. |
| 8,192,628 B2 | 6/2012 | Cranford et al. |
| 8,207,363 B2 | 6/2012 | Apt et al. |
| 9,738,851 B2 | 8/2017 | Ruecker et al. |
| 2002/0037303 A1 | 3/2002 | Deckers et al. |
| 2003/0054084 A1 | 3/2003 | Hruschka et al. |
| 2003/0060509 A1 | 3/2003 | Elswyk |
| 2005/0115897 A1 | 6/2005 | Dueppen et al. |
| 2005/0170479 A1 | 8/2005 | Kobzeff et al. |
| 2005/0239199 A1 | 10/2005 | Kunas et al. |
| 2006/0099693 A1 | 5/2006 | Kobzeff et al. |
| 2007/0003686 A1 | 1/2007 | Fichtali et al. |
| 2007/0077341 A1 | 4/2007 | Schlegel et al. |
| 2007/0138094 A1 | 6/2007 | Bomberger et al. |
| 2007/0213298 A1 | 9/2007 | Rongved et al. |
| 2008/0020124 A1 | 1/2008 | Kawashima et al. |
| 2008/0026103 A1 | 1/2008 | Fichtali et al. |
| 2008/0038800 A1 | 2/2008 | Ruecker et al. |
| 2008/0044875 A1 | 2/2008 | Ruecker et al. |
| 2008/0044876 A1 | 2/2008 | Ruecker et al. |
| 2008/0088489 A1 | 4/2008 | Moon |
| 2008/0107791 A1 | 5/2008 | Fichtali et al. |
| 2008/0148433 A1 | 6/2008 | Metz et al. |
| 2008/0206379 A1 | 8/2008 | Fabritius et al. |
| 2009/0061067 A1 | 3/2009 | Tilseth et al. |
| 2009/0117194 A1 | 5/2009 | Burja et al. |
| 2009/0221705 A1 | 9/2009 | Rongved et al. |
| 2009/0275658 A1 | 11/2009 | Fabritius |
| 2010/0069492 A1 | 3/2010 | Geiringen et al. |
| 2010/0226977 A1 | 9/2010 | Tilseth |
| 2010/0227042 A1 | 9/2010 | Penet et al. |
| 2010/0233761 A1 | 9/2010 | Czartoski et al. |
| 2010/0239533 A1 | 9/2010 | Apt et al. |
| 2010/0239712 A1 | 9/2010 | Brooks et al. |
| 2010/0261918 A1 | 10/2010 | Chianelli et al. |
| 2011/0077031 A1 | 3/2011 | Kim et al. |
| 2011/0086386 A1 | 4/2011 | Czartoski et al. |
| 2011/0159167 A1 | 6/2011 | Ruesing et al. |
| 2011/0179699 A1 | 7/2011 | D'Addario et al. |
| 2011/0201063 A1 | 8/2011 | Mitropoulos |
| 2011/0251278 A1 | 10/2011 | Weber et al. |
| 2011/0252696 A1 | 10/2011 | Franklin et al. |
| 2011/0256268 A1 | 10/2011 | Franklin et al. |
| 2011/0263709 A1 | 10/2011 | Hutchenson et al. |
| 2011/0283602 A1 | 11/2011 | Gallop et al. |
| 2011/0295028 A1 | 12/2011 | Cherinko et al. |
| 2012/0022278 A1 | 1/2012 | Aravanis et al. |
| 2012/0036767 A1 | 2/2012 | Larach |
| 2012/0040428 A1 | 2/2012 | Reep et al. |
| 2012/0040443 A1 | 2/2012 | Wase et al. |
| 2012/0095246 A1 | 4/2012 | Schaap et al. |
| 2012/0119862 A1 | 5/2012 | Franklin et al. |
| 2012/0130099 A1 | 5/2012 | Wittenberg et al. |
| 2012/0135479 A1 | 5/2012 | Dillon et al. |
| 2012/0190872 A1 | 7/2012 | Cranford et al. |
| 2012/0238732 A1 | 9/2012 | Wang |
| 2012/0244584 A1 | 9/2012 | Zhang et al. |
| 2013/0129775 A1 | 5/2013 | Shinde et al. |
| 2013/0210093 A1 | 8/2013 | Pottathil et al. |
| 2014/0212936 A1 | 7/2014 | Ruecker et al. |
| 2015/0176042 A1 | 6/2015 | Dennis et al. |
| 2016/0002566 A1 | 1/2016 | Vanhercke et al. |
| 2016/0010026 A1 | 1/2016 | Dennis et al. |

FOREIGN PATENT DOCUMENTS

| | | |
|---|---|---|
| CA | 2397655 A1 | 7/2001 |
| CA | 2611324 A1 | 6/2007 |
| CA | 2801011 A1 | 12/2011 |
| CN | 1374383 A | 10/2002 |
| CN | 1447860 A | 10/2003 |
| CN | 101455240 A | 6/2009 |
| CN | 101985637 A | 3/2011 |
| CN | 101531690 A | 9/2011 |
| CN | 102388988 A | 3/2012 |
| CN | 101224022 A | 10/2012 |
| DE | 2056896 | 8/1971 |
| EP | 0246324 | 7/1986 |
| EP | 0969086 | 1/2000 |
| EP | 0976828 A1 | 2/2000 |
| EP | 1178103 A1 | 2/2002 |
| EP | 1178118 A1 | 2/2002 |
| EP | 1305440 A2 | 5/2003 |
| EP | 1905309 A1 | 4/2008 |
| EP | 1252324 B1 | 10/2010 |
| GB | 808128 | 1/1959 |
| GB | 1466853 | 3/1977 |
| JP | 62278987 | 12/1987 |
| JP | 63304990 | 12/1988 |
| JP | 01098494 | 4/1991 |
| JP | 61170397 | 7/1996 |
| JP | 08-509355 | 10/1996 |
| JP | 08302384 A2 | 11/1996 |
| JP | 09009981 | 1/1997 |
| JP | 2000508888 | 10/1997 |
| JP | 08509355 | 3/1998 |
| JP | 10072590 | 3/1998 |
| JP | 10-512444 | 12/1998 |
| JP | 11116983 | 4/1999 |
| JP | 2000041684 | 7/1999 |
| JP | 11285376 | 10/1999 |
| JP | 2000135096 | 5/2000 |
| JP | 2000245492 A2 | 9/2000 |
| JP | 2008541779 T2 | 11/2008 |
| JP | 2005244966 | 10/2009 |
| JP | 2010500296 T2 | 1/2010 |
| JP | 2013099365 A2 | 5/2013 |
| JP | 2013532964 T2 | 8/2013 |
| KR | 19990046733 | 7/1999 |
| KR | 100995575 | 11/2010 |
| WO | WO1988008025 | 10/1988 |
| WO | WO1991007498 | 5/1991 |
| WO | WO9408467 | 4/1994 |
| WO | WO1996005278 | 2/1996 |
| WO | WO1996021037 | 7/1996 |

(56) References Cited

FOREIGN PATENT DOCUMENTS

| WO | WO1997004121 | | 2/1997 |
|---|---|---|---|
| WO | WO1997036996 | | 10/1997 |
| WO | WO1997037032 | | 10/1997 |
| WO | WO1997043362 | | 11/1997 |
| WO | WO1998003671 | | 1/1998 |
| WO | WO1998039468 | | 9/1998 |
| WO | WO1998050574 | | 11/1998 |
| WO | WO1999032604 | | 7/1999 |
| WO | WO200044862 | | 8/2000 |
| WO | WO2001053512 | A1 | 7/2001 |
| WO | WO2001076385 | A1 | 10/2001 |
| WO | WO2001076715 | A2 | 10/2001 |
| WO | WO2002010423 | | 2/2002 |
| WO | WO2003092628 | A2 | 11/2003 |
| WO | WO2004001021 | A1 | 12/2003 |
| WO | WO2006046943 | | 5/2006 |
| WO | WO2006128244 | A1 | 12/2006 |
| WO | WO2008088489 | A2 | 7/2008 |
| WO | WO2008130372 | A2 | 10/2008 |
| WO | WO2008151373 | A1 | 12/2008 |
| WO | WO20090117869 | A1 | 10/2009 |
| WO | WO2010006765 | | 1/2010 |
| WO | WO2010017243 | A1 | 2/2010 |
| WO | WO2010039030 | A1 | 4/2010 |
| WO | WO2010096002 | A1 | 8/2010 |
| WO | WO2010107415 | A1 | 9/2010 |
| WO | WO2010120939 | A2 | 10/2010 |
| WO | WO2010138620 | A1 | 12/2010 |
| WO | WO2011059745 | A1 | 5/2011 |
| WO | WO2011090493 | A1 | 7/2011 |
| WO | WO2011133181 | A1 | 10/2011 |
| WO | WO2011153246 | A2 | 12/2011 |
| WO | WO2012054404 | A2 | 4/2012 |
| WO | WO2012061647 | A2 | 5/2012 |
| WO | WO2012062962 | A1 | 5/2012 |
| WO | WO2012078852 | A2 | 6/2012 |
| WO | WO2012109642 | A1 | 8/2012 |
| WO | WO2012164211 | A1 | 12/2012 |
| WO | WO2013040732 | A1 | 3/2013 |
| WO | WO2013156720 | A2 | 10/2013 |
| WO | WO2014004999 | A1 | 1/2014 |
| WO | WO2015092544 | A1 | 6/2015 |
| WO | WO2015092546 | A1 | 6/2015 |
| WO | WO2015095462 | A1 | 6/2015 |
| WO | WO2015095688 | A1 | 6/2015 |
| WO | WO2015095690 | A2 | 6/2015 |
| WO | WO2015095693 | A2 | 6/2015 |
| WO | WO2015095694 | A1 | 6/2015 |
| WO | WO2015095696 | A1 | 6/2015 |

OTHER PUBLICATIONS

Alternative Methods of Extraction, Oil & Fats International, 1992, pp. 29-32, Issue 6.
Atkinson et al., Biochemical Engineering and Biotechnology Handbook, 1991, p. 918-923.
Ayres et al., Effect of divalent cations on permeabilizer-induced lysozyme lysis of Pseudomonas aeruginosa, Letters in Applied Microbiology, 1998, p. 372-374, vol. 27, No. 6.
Bailey et al., Canola Oil, Physical and Chemical Properties, 1996, 53.
Baldauf, S.M., Book, Am. Nat., 1999, 154, S178.
Benemann et al., System and Economic Analysis of Microalgae Ponds for Conversion of C02 to Biomass, Final Report to the Department of Energy Technology Center, 1996, pp. 1-27, 124-144.
Benemann, Jr., Oswald, Database Extract of Diaglogue, Government Reports Announcements & Index, 1998, Issue 3.
Cartens et al., Eicosapentaenoic Acid (20:5n-3) from the Marine Microalga Phaeodactylum tricornutum, JAOCS, 1996, pp. 1025-1031, vol. 73, No. 8.
Chen et al., Subcritical co-solvents extraction of lipid from wet microalgae pastes of *Nannochloropsis* sp., Eur. J. Lipid Sci. Technol., 2011, 205-212, 114(2).
Christi et al., Disruption of Microbial Cells for Intracellular Products, Enzyme Microb. Technol., 1986, 194-204, 8.
Doisaki, Nobushige, Doisaki, Nobushige Declaration, dated Apr. 10, 2012, 2012.
Ellenbogen et al., Polyunsaturated Fatty Acids of Aquatic Fungi: Possible Phylogenetic Significance, Comp. Biochem. Physiol., 1969, 805-811, 29.
Enssani, E., Fundamental Parameters in Extraction of Lipids from Wastewater-grown Microalgal Biomass, Dissertation Thesis, Department of Civil Engineering, 1987, University of California, Berkeley.
EPO, Extended European Search Report EP2266525, dated Nov. 24, 2010, 2010.
European Search Report dated Jul. 30, 2004, EP1252324.
Graille et al., Biotechnology of Lipids: Some Possible Applications, Oleagineux, 1988, pp. 181-190, 43(4).
GRAS Exemption Claim for Docosahexaenoic Acid Rich Oil Derived from Tuna (DHA-rich oil) and Arachidonic Acid Rich Oil Derived from Mortierella alpine Peyronel 1S-4 (M. alpine) (AA-rich oil; SUNTGA40S) as Sources of DHA and AA in Term and Preterm Infant Formulas dated Dec. 18, 2001.
Gunstone et al., The Lipid Handbook, Second Edition, 1995, 258-261.
Harrison et al., Combined Chemical and Mechanical Processes for the Disruption of Bacteria, Bioseparation, 1991, pp. 95-105, 2(2).
Higuchi et al., Pro-drugs as Noval Delivery Systems, ACS Symposum Series, 1975, Book, American Chemical Society.
Honda et al., Molecular Phylogeny of Labyrinthulids and Thraustochytrids based on the Sequencing of 18S Ribosomal RNA Gene, Journal of Eukaryotic Microbiology, 1999, pp. 637-647, 46(6).
Honda et al., *Schizochytrium limacinum* sp. nov., a new thraustochytrid from a mangrove area in the west Pacific Ocean, Mycol Res., 1998, 43-448, 102(4), Cambridge University Press for the British Mycological Society, England.
Hruschika et al., New Oil Extraction Process: FRIOLEX, OCL, 1998, 356-360, 5(5).
International Searching Authority, Written Opinion of the ISA, WO2006046943, dated 2007.
Jagannadham et al., The Major Carotenoid Pigment of a Psychotrophic Microoccus roseau Strain: Purification, Structure, and Interaction with Synthetic Members, American Society for Microbiology, 1991, 7911-7917, 173(24).
Jin et al., Enzyme Assisted Extraction of Lipids Directly from the Culture of the Oleaginous Yeast Rhodosporidium toruloides, Bioresource Technology, 2012, 378-382, 111.
KIPO, Decision of Korean IP Office in KR2010-7008702, KR20107008702, English Translation.
KIPO, KR20107027153 Office Action dated Mar. 10, 2011.
KIPO, Notification of Opinion Submission for KR2010-7008702 dated Aug. 17, 2010, KR20107008702.
KIPO, Trial Decision dated Nov. 30, 2012 in Appeal against the decision of rejection concerning KR2010-7008702, KR20107008702.
Kyle et al., Industrial Applications of Single Cell Oils, 1992, US.
Lin et al., Efficiency of Removing Volatiles from Menhaden Oils by Refining, Bleaching, and Deodorization, Journal of Food Science, 1990, 1669-1672, 55(6).
List et al., Oxidation and Quality of Soybean Oil: A Preliminary Study of the Anisidine Test, J. Am. Oil. Chem. Soc., 1974, 17-21, 51.
MacFarlane 2001, The Fast Index—Fishy Scale, A Search for a Test to Quanity Fish Flavor, 2001, 244-249, 12.
Margulis et al., Evaluation of Fungicides for Control of Rapid Blight of Poa Trivialis, Handbook of Protoctista, 1994, 388-398 (Abstract).
Mcomie, J.F., Protective Groups in Organic Chemistry, Book, 1973, Plenum Press, New York.
Medina et al., Downstream Processing of Algal Polyunsaturated Fatty Acids, Biotechnology Advances, 1998, 517-580, 16(3).
Mercer, Paula et al., Developments in oil extraction from microalgae, Eur. J. Lipid Sci. Technol., 2011, 1-9.
Middelberg, Anton, Process-Scale Disruption of Microorganisms, Biotechnology Advances, 1995, 491-551, 13(3).

(56) References Cited

OTHER PUBLICATIONS

Miura et al., Production of the Carotenoids Lycopene, B-Carotene, and Astaxanthin in the Food Yeast Candida utilis, Applied and Environmental Microbiology, 1998, 1226-1229, 64(4).

Myber et al., Stereospecific Analysis of Triacylglycerols Rich in Long-Chain Polyunsaturated Fatty Acids, Lipids, 1996, p. 207-215, 31(2), US.

N/A, Public Disclosure, Federal Register, 1997, n/a, 62(74), US.

Notice of Opposition for EP1252324 dated Jul. 19, 2011, English Translation.

Papanikolaou et al., Lipids of Oleaginous yeasts, Part II: Technology and Potential Applications, Eur. J. Lipid Sci. Technol., 2011, 1052-1073, 113.

Pena et al., Rehydration temperature is critical for metabolic competence and for membrane integrity in active dry yeast, Arch Microbiol, 1992, 75-80, 158.

Preez et al., Production of Gamma-Linolenic Acid by Mucor Circinelloides and Mucor Rouxii with Acetic Acid as Carbon Substrate, Biotechnology Letter, 1995, 933-938, 17(9).

Privett, Preparation of Polyunsaturated Fatty Acids from Natural Sources, Progr. Chem. Fats Lipids, 1968, 407-452, 9(P43).

Qi et al., Production of DHA by a Method of Fermentation of Marine Microalgae, Science and Technology of Food Industry, 1999, 62-63, Section 4, 20(6).

Redman, Colvin, Phospholipid metabolism in intact and modified erythrocyte membrane, The Journal of Cell Biology, 1971, 35-49, 49(1).

Roche, Edward B., Bioreversible Carriers in Drug Design, Theory and Application, 1987, 13-94, Book, American Pharmaceutical Association, Pergamon.

Roodbari et al., Tweens demulsification effects on heavy crude oil/water emulsion, Arabian Journal of Chemistry, 2011, 1-6.

Rosenthal et al., "Aqueous and enzymatic processes for edible oil extraction", Enzyme and Microbial Technology, vol. 19, pp. 402-420 (1996).

Sambrook et al., Molecular Cloning: A Laboratory Manual, Book, 2001.

Sawayama et al., Possibility of renewable energy production of CO2 mitigation by thermochemical liquefaction of microalgae, Biomass and Bioenergy, 1999, 33-39, 17.

Seher, A., Sterols in the chemistry and technology of edible fats and oils, Lipids, 1976, N/A, 2, US.

Totani et al., Indsutrial Production of Arachidonic Acid by Mortierella, 1992, 52-60, (4).

USPTO, Office Action dated Apr. 14, 2010, U.S. Appl. No. 10/971,723, 2010.

USPTO, Office Action dated Dec. 1, 2008, U.S. Appl. No. 10/513,576, 2008.

USPTO, Office Action dated Dec. 15, 2008, U.S. Appl. No. 10/971,723, 2008.

USPTO, Office Action dated Feb. 21, 2008, U.S. Appl. No. 10/971,723, 2008.

USPTO, Office Action dated Jul. 3, 2007, U.S. Appl. No. 10/971,723, 2007.

USPTO, Office Action dated Jun. 1, 2009, U.S. Appl. No. 10/513,576, 2009.

USPTO, Office Action dated Mar. 1, 2010, U.S. Appl. No. 10/513,576, 2010.

USPTO, Office Action dated Mar. 19, 2009, U.S. Appl. No. 10/971,723, 2009.

USPTO, Office Action dated May 14, 2008, U.S. Appl. No. 10/513,576, 2008.

USPTO, Office Action dated Jul. 22, 2009, U.S. Appl. No. 10/971,723, 2009.

Vazhappilly et al., Eicosapentaenoic Acid and Docosahexaenoic Acid Production Potential of Microalgae and their Heterotrophic Growth, JAOCS, 1998, 393-397, 75(3).

Weete et al., Sterols and fatty acids of the Mortierellaceae: taxonomic implications, Mycologia, 1999, 642-649, 91(4), US.

WIPO, International Search Report WO2003092628, dated Nov. 3, 2003, 2003.

WIPO, International Search Report WO2006046943, dated Sep. 26, 2007, 2007.

WIPO, IPER dated May 6, 2002, WO2001001806.

WIPO, IPER dated Sep. 27, 2002, WO2001001806.

WIPO, IPER WO2003092628, dated Feb. 21, 2005, 2005.

WIPO, IPER WO2006046943, dated Dec. 27, 2007, 2007.

WIPO, ISR WO2001001806, May 22, 2001.

WIPO, WO2006046943 Communication in which no other form available, dated Oct. 31, 2007, 2007.

Written Opinion dated Sep. 25, 2001, WO2001001806.

Wynn et al., The role of malic enzyme in the regulation of lipid accumulation in filamentous fungi, Microbiology, 1999, 1911-1917, 145.

Yokoyama et al., Taxonomic rearrangement of the genus *Ulkenia sensu* lato based on morphology, chemotaxonomical characteristics, and 18S rRNA gene phylogeny: emendation for Ulkenia and erection of *Botryochytrium, Parietichytrium*, and *Sicyoidochytrium* gen. nov., Mycoscience, 2007, 329-341, 48.

Zhan et al., Chemosynthesis of Squalene, DHA and EPA in Sea Fish Oil, Sichuan Chemiical Industry and Corrosion, 1999, 38-43, 2(2).

Zhang et al., Acqueous enzymatic extraction technology of oil and protein hydrolysates from rapeseed, Transactions of the CSAE, 2007, 213-219, 23(9).

Zhang et al., Mechanism of lipid extractionf rom biotryoccus braunii FACHB 357 in the biphasic bioreactor, Science Direct, 2011, pp. 281-284, vol. 154, Issue 4.

Zhang et al., Production of Docosahexaenoic Acid by Oceanic Microorganism, Marine Science Bulletin, 1999, pp. 88-92, vol. 18, No. 1.

Zhang et al., Screening of biocompatible organic solvents for enhancement of lipid milking from *Nannochloripsis* sp., Science Direct, 2011, pp. 1934-1941, vol. 46, Issue 10.

Zhu et al., Extraction of lipid from sea urchin gonad by enzyme-assisted aqueous and supercritical carbon dioxide methods., Eur. Food Research Technology, 2010, pp. 737-743, vol. 230.

Anonymous, Food Standards Australia New Zealand, Dhasco and arasco oils as sources of long-chain polyunsaturated fatty acids in infant formula, 2003, 3-50, 22.

Cuellar-Bermudez et al., Extraction and Purification of high-value metabolites from microalgae: essential lipids, astaxanthin and phycobiliproteins, Microbial Biotechnology, 2014, 190-209, 8.

Kamisaka et al, J. Biochem., Characterization of the Diacylglycerol Acyltransferase Activity in the Lipid Body Fraction from an Oleaginous Fungus, 1994, 1295-1301, 116.

Liu Guangcheng, Several Demulsifying Methods, China Surfactant Detergent & Cosmetics, Dec. 31, 1983, 49-50.

Lowrey, Joshua, Nutrient recylcing of lipid-extracted waste in the production of an oleaginous thraustochytrid, Appl Microbiol Biotechnol, 2016, 4711-4721, 100.

Olofsson et al., Seasonal Variation of Lipids and Fatty Acids of the Microalgae *Nannochloropsis oculata* Grown in Outdoor Large-Scale Photobioreactors, Energies, 2012, 1577-1592, 5(12).

Thakur et al., De Novo Transciptome Sequencing and Analysis for Venturia inaequalis, the Devastating Apple Scab Pathogen, Plos One, Jan. 2013, vol. 8 / Issue 1.

You et al., Enzymatic hydrolysis and extraction of arachidonic acid rich lipids from Mortierella Alpina, Bioresource Technology, 2011, 6088-6094, 102.

ATCC, ATCC 20891, 20891, 2018, http://www.atcc.org/products/all/20891.aspx.

Liang et al., Enzyme-Assisted Aqueous Extraction of Lipid from Microalgae, Journal of Agricultural and Food Chemistry, 2012, 11771-6, 60(47).

Lowrey et al., Sequential Recycling of Enzymatic Lipid-Extracted Hydrolysate in Fermentations with a Thraustochytrid, Bioresource Technology, 2016, 333-342, 209.

Mankowich et al., Coating and Chemical Laboratory, CCL Report No. 137, 1963, 1-26.

Ratledge et al., Down-stream processing, extraction, and purification of single cell oils, Single Cell Oils, 2005, 202-219, Chapter 13.

(56) References Cited

OTHER PUBLICATIONS

Xia et al., Chemical Abstracts 2009, Preparation of virgin coconut oil by cellulase hydrolysis, 2009.
Grenville et al., Mixing: Impeller Performance in Stirred Tanks, Chemical Engineering, Aug. 2017, 42-51, US.
Particles Sciences 2009, Emulsions and Emulsification, Particles Sciences, 2009, 1-2, 9, US.
Cooney et al., Extraction of Bio-oils from Microalgae, Separation & Purification Reviews, 2009, 291-325, 38(4).
Milledge et al., A Review of the Harvesting of Micro-Algae for Biofuel Productio, Reviews in Environmental Science and Biotechnology, 2013, 165-78, 12(2).

PROCESSES FOR OBTAINING MICROBIAL OIL FROM MICROBIAL CELLS

CROSS REFERENCE TO RELATED APPLICATIONS

This application claims the benefit of the filing date of U.S. Provisional Patent Application No. 61/918,922 filed Dec. 20, 2013, the disclosure of which is hereby incorporated herein by reference.

BACKGROUND OF THE INVENTION

Disclosed herein are processes for obtaining microbial oil comprising one or more polyunsaturated fatty acids (PUFAs) from one or more microbial cells by lysing the cells to form a lysed cell composition and then recovering the oil from the lysed cell composition. Further disclosed herein is microbial oil comprising one or more PUFAs that is recovered from microbial cells by at least one process described herein.

Microbial oil containing one or more PUFAs is produced by microorganisms, such as, for example, algae and fungi.

A typical process for obtaining PUFA containing oil from microbial cells involves growing microorganisms that are capable of producing the desired oil in a fermentor, pond or bioreactor to produce a microbial cell biomass; separating the biomass from the fermentation medium in which the biomass was grown; drying the microbial cell biomass, using a water-immiscible organic solvent (e.g., hexane) to extract the oil from the dried cells; and removing the organic solvent (e.g., hexane) from the oil. This process can further involve diluting the fermentation medium containing the cell biomass with water followed by centrifugation to separate the biomass from the diluted fermentation medium.

Another process for obtaining PUFA containing oil from microbial cells involves growing microorganisms that are capable of producing the desired oil in a fermentor, pond or bioreactor to produce a microbial cell biomass; releasing the PUFA containing oil into the fermentation medium in which the cells were grown by using mechanical force (e.g., homogenization), enzymatic treatment, or chemical treatment to disrupt the cell walls; and recovering the oil from the resulting composition comprising PUFA containing oil, cell debris, and liquid using an water miscible organic solvent, e.g., isopropyl alcohol. The oil can be separated mechanically from the composition and the alcohol must be removed from both the oil and the aqueous biomass waste stream.

The industrial scale employment of either of the above processes for obtaining PUFA containing oils from microbial cells requires the use of a large amount of volatile and flammable organic solvent, which creates hazardous operating conditions and requires the use of expensive explosion-proof equipment. Additionally, the use of an organic solvent generates an organic solvent waste stream that requires implementation of an expensive solvent recovery process to address the strict environmental limits on volatile organic compound (VOC) emissions, which in turn results in the need for more manpower and costly equipment.

Further, the use of heat in the above processes to dry the cells and/or remove the solvent from the recovered oil can degrade the PUFA containing oils and increase energy usage, which can further increase processing costs. Degradation occurs when PUFA containing oils are exposed to oxygen such as when the integrity of the microbial cell walls is disrupted and/or the microbial cells are exposed to heat.

A solvent-free process for obtaining PUFA containing oil from microbial cells involves growing microorganisms that are capable of producing the desired oil in a fermentor, pond or bioreactor to produce a microbial cell biomass; releasing the PUFA containing oil into the fermentation medium in which the cells were grown by using mechanical force (e.g., homogenization), enzymatic treatment, or chemical treatment to disrupt the cell walls; and recovering crude oil from the resulting composition comprising PUFA containing oil, cell debris, and liquid by raising the pH, adding a salt, heating, and/or agitating the resulting composition. This solvent-free process for obtaining PUFA containing oil from cells, however, can require long oil recovery times, large amounts of salt, and/or many steps, which can all increase processing costs.

As a result, there remains a need for a process for obtaining high quality PUFA containing oils from microbial cells that does not use a volatile organic solvent, can be performed using readily available equipment, requires a minimum number of steps, has shorter oil recovery times, and can provide a high yield of high quality PUFA containing oil.

Disclosed herein is a process for obtaining a microbial oil comprising one or more polyunsaturated fatty acids (PUFAs) from one or more microbial cells comprising (a) lysing the cells comprising the microbial oil to form a lysed cell composition; (b) demulsifying the lysed cell composition comprising lowering the pH of the lysed cell composition to form a demulsified lysed cell composition; (c) separating the oil from the demulsified lysed cell composition; and (d) recovering the oil.

Disclosed herein is a process for obtaining a microbial oil comprising one or more polyunsaturated fatty acids (PUFAs) from one or more microbial cells comprising (a) lysing the cells comprising the microbial oil to form a lysed cell composition; (b) demulsifying the lysed cell composition comprising lowering the pH of the lysed cell composition to about 6 or less to form a demulsified lysed cell composition; (c) separating the oil from the demulsified lysed cell composition; and (d) recovering the oil.

Disclosed herein is a process for obtaining a microbial oil comprising one or more polyunsaturated fatty acids (PUFAs) from one or more microbial cells comprising (a) lysing the cells comprising the microbial oil to form a lysed cell composition; (b) demulsifying the lysed cell composition comprising lowering the pH of the lysed cell composition by adding an acid in an amount of from about 0.5% to about 20%, by weight, lysed cell composition to form a demulsified lysed cell composition; (c) separating the oil from the demulsified lysed cell composition; and (d) recovering the oil.

Disclosed herein is a process for obtaining a microbial oil comprising one or more polyunsaturated fatty acids (PUFAs) from one or more microbial cells comprising (a) lysing the cells comprising the microbial oil to form a lysed cell composition; (b) demulsifying the lysed cell composition comprising lowering the pH of the lysed cell composition to about 6 or less to form a demulsified lysed cell composition; (c) separating the oil from the demulsified lysed cell composition; and (d) recovering the oil, where at least one of (a) or (b) further comprises heating the composition to a temperature of at least 70° C.

Disclosed herein is a process for obtaining a microbial oil comprising one or more polyunsaturated fatty acids (PUFAs) from one or more microbial cells comprising (a) lysing the cells comprising the microbial oil to form a lysed cell composition; (b) demulsifying the lysed cell composition comprising lowering the pH of the lysed cell composition by adding an acid in an amount of from about 0.5% to about 20%, by weight, lysed cell composition to form a demulsified lysed cell composition; (c) separating the oil from the demulsified lysed cell composition; and (d) recovering the oil, where at least one of (a) or (b) further comprises heating the composition to a temperature of at least 70° C.

Disclosed herein is a process for obtaining a microbial oil comprising one or more polyunsaturated fatty acids (PUFAs) from one or more microbial cells comprising (a) lysing the cells comprising the microbial oil to form a lysed cell composition; (b) demulsifying the lysed cell composition comprising adding an acid to lower the pH of the lysed cell composition to about 6 or less and agitating the lysed cell composition to form a demulsified lysed cell composition; (c) separating the oil from the demulsified lysed cell composition; and (d) recovering the oil.

Disclosed herein is a process for obtaining a microbial oil comprising one or more polyunsaturated fatty acids (PUFAs) from one or more microbial cells comprising (a) lysing the cells comprising the microbial oil to form a lysed cell composition; (b) demulsifying the lysed cell composition comprising lowering the pH of the lysed cell composition to form a demulsified lysed cell composition; (c) separating the oil from the demulsified lysed cell composition; and (d) recovering the oil, where (a) and (b) are combined together to form a one-step lysing and demulsifying step.

Disclosed herein is a process for obtaining a microbial oil comprising one or more polyunsaturated fatty acids (PUFAs) from one or more microbial cells comprising (a) lysing the cells comprising the microbial oil to form a lysed cell composition; (b) demulsifying the lysed cell composition to form a demulsified lysed cell composition; (c) separating the oil from the demulsified lysed cell composition; and (d) recovering the oil, where (a) and (b) are combined together to form a one-step lysing and demulsifying step that comprises raising the pH.

Disclosed herein is a process for obtaining a microbial oil comprising one or more polyunsaturated fatty acids (PUFAs) from one or more microbial cells comprising (a) lysing the cells comprising the microbial oil at a pH suitable to form a demulsified lysed cell composition; (b) separating the oil from the demulsified lysed cell composition; and (c) recovering the oil, wherein the demulsified lysed cell composition is obtained during the lysing.

Disclosed herein is a microbial oil obtained by any of the processes described herein.

Polyunsaturated fatty acids (PUFAs) are classified based on the position of the first double bond from the methyl end of the fatty acid; omega-3 (n-3) fatty acids contain a first double bond at the third carbon, while omega-6 (n-6) fatty acids contain a first double bond at the sixth carbon. For example, docosahexaenoic acid (DHA) is an omega-3 long chain polyunsaturated fatty acid (LC-PUFA) with a chain length of 22 carbons and 6 double bonds, often designated as "22:6n-3." In one embodiment, the PUFA is selected from an omega-3 fatty acid, an omega-6 fatty acid, and mixtures thereof. In another embodiment, the PUFA is selected from LC-PUFAs. In a still further embodiment, the PUFA is selected from docosahexaenoic acid (DHA), eicosapentaenoic acid (EPA), docosapentaenoic acid (DPA), arachidonic acid (ARA), gamma-linolenic acid (GLA), dihomo-gamma-linolenic acid (DGLA), stearidonic acid (SDA), and mixtures thereof. In another embodiment, the PUFA is selected from DHA, ARA, and mixtures thereof. In a further embodiment, the PUFA is DHA. In yet a further embodiment, the PUFA is ARA.

LC-PUFAs are fatty acids that contain at least 3 double bonds and have a chain length of 18 or more carbons or 20 or more carbons. LC-PUFAs of the omega-6 series include, but are not limited to, di-homo-gammalinoleic acid (C20:3n-6), arachidonic acid (C20:4n-6) ("ARA"), docosatetraenoic acid or adrenic acid (C22:4n-6), and docosapentaenoic acid (C22:5n-6) ("DPA n-6"). The LC-PUFAs of the omega-3 series include, but are not limited to, eicosatrienoic acid (C20:3n-3), eicosatetraenoic acid (C20:4n-3), eicosapentaenoic acid (C20:5n-3) ("EPA"), docosapentaenoic acid (C22:5n-3), and docosahexaenoic acid (C22:6n-3). The LC-PUFAs also include fatty acids with greater than 22 carbons and 4 or more double bonds including, but not limited to, C24:6(n-3) and C28:8(n-3).

The PUFAs can be in the form of a free fatty acid, salt, fatty acid ester (e.g. methyl or ethyl ester), monoacylglycerol (MAG), diacylglycerol (DAG), triacylglycerol (TAG), and/or phospholipid (PL).

Highly unsaturated fatty acids (HUFAs) are omega-3 and/or omega-6 polyunsaturated fatty acids that contain 4 or more unsaturated carbon-carbon bonds.

As used herein, a "cell" refers to an oil-containing biomaterial, such as biomaterial derived from oleaginous microorganisms. Oil produced by a microorganism or obtained from a microbial cell is referred to as "microbial oil". Oil produced by algae and/or fungi is also referred to as algal and/or fungal oil, respectively.

As used herein, a "microbial cell" or "microorganism" refers to organisms such as algae, bacteria, fungi, protist, yeast, and combinations thereof, e.g., unicellular organisms. In some embodiments, a microbial cell is a eukaryotic cell. A microbial cell includes, but is not limited to, golden algae (e.g., microorganisms of the kingdom Stramenopiles); green algae; diatoms; dinoflagellates (e.g., microorganisms of the order *Dinophyceae* including members of the genus *Crypthecodinium* such as, for example, *Crypthecodinium cohnii* or *C. cohnii*); microalgae of the order Thraustochytriales; yeast (Ascomycetes or Basidiomycetes); and fungi of the genera *Mucor*, *Mortierella*, including but not limited to *Mortierella alpina* and *Mortierella* sect. *schmuckeri*, and *Pythium*, including but not limited to *Pythium insidiosum*.

In one embodiment, the microbial cells are from the genus *Mortierella*, genus *Crypthecodinium*, or order Thraustochytriales. In a still further embodiment, the microbial cells are from *Crypthecodinium Cohnii*. In yet an even further embodiment, the microbial cells are selected from *Crypthecodinium Cohnii*, *Mortierella alpine*, genus *Thraustochytrium*, genus *Schizochytrium*, and mixtures thereof.

In a still further embodiment, the microbial cells include, but are not limited to, microorganisms belonging to the genus *Mortierella*, genus *Conidiobolus*, genus *Pythium*, genus *Phytophthora*, genus *Penicillium*, genus *Cladosporium*, genus *Mucor*, genus *Fusarium*, genus *Aspergillus*, genus *Rhodotorula*, genus *Entomophthora*, genus *Echinosporangium*, and genus *Saprolegnia*. In another embodiment, ARA is obtained from microbial cells from the genus *Mortierella*, which includes, but is not limited to, *Mortierella elongata*, *Mortierella exigua*, *Mortierella hygrophila*, *Mortierella alpina*, *Mortierella schmuckeri*, and *Mortierella minutissima*. In a further embodiment, ARA is obtained from microbial cells from *Mortierella elongata* IFO8570, *Mortierella exigua* IFO8571, *Mortierella hygrophila* IFO5941, *Mortierella alpina* IFO8568, ATCC16266, ATCC32221, ATCC42430, CBS219.35, CBS224.37, CBS250.53, CBS343.66, CBS527.72, CBS529.72, CBS608.70, and CBS754.68, and mutants thereof. In a still further embodiment, the microbial cells are from *Mortierella alpina*.

In an even further, the microbial cells are from microalgae of the order Thraustochytriales, which includes, but is not limited to, the genera *Thraustochytrium* (species include *arudimentale, aureum, benthicola, globosum, kinnei, motivum, multirudimentale, pachydermum, proliferum, roseum, striatum*); the genera *Schizochytrium* (species include *aggregatum, limnaceum, mangrovei, minutum, octosporum*); the genera *Ulkenia* (species include *amoeboidea, kerguelensis, minuta, profunda, radiate, sailens, sarkariana, schizochytrops, visurgensis, yorkensis*); the genera *Aurantiacochytrium*; the genera *Oblongichytrium*; the genera *Sicyoidochytium*; the genera *Parientichytrium*; the genera *Botryochytrium*; and combinations thereof. Species described within *Ulkenia* will be considered to be members of the genus *Schizochytrium*. In another embodiment, the microbial cells are from the order Thraustochytriales. In yet another embodiment, the microbial cells are from *Thraustochytrium*. In still a further embodiment, the microbial cells are from *Schizochytrium*. In a still further embodiment, the microbial cells are chosen from genus *Thraustochytrium*, *Schizochytrium*, or mixtures thereof.

In one embodiment, the process comprises lysing microbial cells comprising a microbial oil to form a lysed cell composition. The terms "lyse" and "lysing" refer to a process whereby the wall and/or membrane of the microbial cell is ruptured. In one embodiment, the microbial cell is lysed by being subjected to at least one treatment selected from mechanical, chemical, enzymatic, physical, and combinations thereof. In another embodiment, the process comprises lysing the microbial cells comprising the microbial oil to form a lysed cell composition, wherein the lysing is selected from mechanical, chemical, enzymatic, physical, and combinations thereof.

In some embodiments, prior to lysing the cell, the cell can be washed and/or pasteurized. In some embodiments, washing the cells includes using an aqueous solution, such as water, to remove any extracellular water-soluble or water-dispersible compounds. In some embodiments, the cell can be washed once, twice, thrice, or more. In some embodiments, pasteurizing the cell includes heating the cell to inactivate any undesirable enzymes, for example any enzymes that might degrade the oil or reduce the yield of PUFAs. In some embodiments, the cell is washed and then pasteurized before being lysed. In some embodiments, the cells that are being lysed are contained in a fermentation broth.

In some embodiments, the process comprises lysing unwashed microbial cells comprising a microbial oil to form a lysed cell composition. In some embodiments, a fermentation broth comprising microbial cells comprising microbial oil is first washed with, for example, water and then the cells lysed to form a lysed-cell composition. In other embodiments, the process comprises lysing unwashed cells in a fermentation medium to form a lysed cell composition.

Mechanical treatment includes, but is not limited to, homogenization, ultrasound, cold-pressing, milling, and combinations thereof. In some embodiments, the process comprises lysing the cells by homogenization. In some embodiments, the process comprises lysing the cell with a homogenizer.

Homogenization includes, but is not limited to, processes that utilize a French cell press, sonicator, homogenizer, microfluidizer, ball mill, rod mill, pebble mill, bead mill, high pressure grinding roll, vertical shaft impactor, industrial blender, high shear mixer, paddle mixer, polytron homogenizer, industrial homogenizer (e.g., Niro Soavi VHP Homogenizer and APV Rannie and APV Gaulin homogenizers), Industrial high shear fluid processors (e.g., Microfluidics high shear fluid processor), cell lysing/bead mill homogenizers (e.g., Dyno-Mill and Buhler), and combinations thereof. In some embodiments, the cells flow through a homogenizer that is optionally heated. In some embodiments, suitable homogenization can include 1 to 3 passes through a homogenizer at either high and/or low pressures.

In some embodiments, the pressure during homogenization is 150 bar to 1,400 bar; 150 bar to 1,200 bar; 150 bar to 900 bar; 150 bar to 300 bar; 300 bar to 1,400 bar; 300 bar to 1,200 bar; 300 bar to 900 bar; 400 bar to 800 bar; 500 bar to 700 bar; or 600 bar. In some embodiments, the pressure during homogenization is 2,000 psi to 20,000 psi; 2,000 psi to 18,000 psi; 2,000 psi to 16,000 psi; 2,000 psi to 14,000 psi; 2,000 psi to 12,000 psi; 2,000 psi to 10,000 psi; 2,000 psi to 8,000 psi; 2,000 psi to 6,000 psi; 2,000 psi to 4,000 psi; 4,000 psi to 20,000 psi; 4,000 psi to 18,000 psi; 4,000 psi to 16,000 psi; 4,000 psi to 14,000 psi; 4,000 psi to 12,000 psi; 4,000 psi to 10,000 psi; 4,000 psi to 8,000 psi; 4,000 psi to 6,000 psi; 6,000 psi to 20,000 psi; 6,000 psi to 18,000 psi; 6,000 psi to 16,000 psi; 6,000 psi to 14,000 psi; 6,000 psi to 12,000 psi; 6,000 psi to 10,000 psi; 6,000 psi to 8,000 psi; 8,000 psi to 20,000 psi; 8,000 psi to 18,000 psi; 8,000 psi to 16,000 psi; 8,000 psi to 14,000 psi; 8,000 psi to 12,000 psi; 8,000 psi to 10,000 psi; 10,000 psi to 20,000 psi; 10,000 psi to 18,000 psi; 10,000 psi to 16,000 psi; 10,000 psi to 14,000 psi; 10,000 psi to 12,000 psi; 12,000 psi to 20,000 psi; 12,000 psi to 18,000 psi; 12,000 psi to 16,000 psi; 12,000 psi to 14,000 psi; 14,000 psi to 20,000 psi; 14,000 psi to 18,000 psi; 14,000 psi to 16,000 psi; 16,000 psi to 20,000 psi; 16,000 psi to 18,000 psi; or 18,000 psi to 20,000 psi.

In some embodiments, the microbial cells are mixed in high shear mixer before being homogenized. In some embodiments, the high shear mixer is operated in a range of at least 5,000 rpm; at least 7,500 rpm; at least 10,000 rpm; at least 12,500 rpm; at least 15,000 rpm; 5,000 rpm to 15,000 rpm; 5,000 rpm to 12,500 rpm; 5,000 rpm to 10,000 rpm; 5,000 rpm to 7,500 rpm; 7,500 rpm to 15,000 rpm; 7,500 rpm to 12,500 rpm; 7,500 rpm to 10,000 rpm; 10,000 rpm to 15,000 rpm; 10,000 rpm to 12,500 rpm; or 12,500 rpm to 15,000 rpm.

Physical treatment includes, but is not limited to, heating, which includes, but is not limited to, resistive, convection, steam, fluid bath, solar, and combinations thereof. In some embodiments, the cells are heated in a tank with resistive coils in/on its walls. In some embodiments, the cells are heated in a liquid bath with tubes passing there through.

Chemical treatment includes, but is not limited to, raising the pH of the cells; lowering the pH of the cells; contacting the cells with a chemical; and combinations thereof.

In some embodiments, the cells are lysed by raising the pH of the cells. In some embodiments, the pH is raised by adding a base. The bases include, but are not limited to, hydroxides (e.g., LiOH, NaOH, KOH, and Ca(OH)$_2$, and combinations thereof); carbonates (e.g., Na$_2$CO$_3$, K$_2$CO$_3$, MgCO$_3$, and combinations thereof); bicarbonates (e.g., LiHCO$_3$, NaHCO$_3$, KHCO$_3$, and combinations thereof); and combinations thereof. The base can be in the form of a solid (e.g., crystals, granulates, and pellets); a liquid (e.g., an aqueous solution); and combinations thereof.

In some embodiments, the base has a pK$_b$ of 1 to 12, 1 to 10, 1 to 8, 1 to 6, 1 to 5, 2 to 12, 2 to 10, 2 to 8, 2 to 6, 2 to 5, 3 to 10, 3 to 6, 3 to 5, 4 to 10, 4 to 8, 4 to 6, 5 to 10, or 5 to 8. As used herein, the term "pK$_b$" refers to the negative logarithm of the base association constant, $K_b$, of the base. $K_b$ refers to the equilibrium constant for the ionization of the base in water, wherein:

$B+H_2O \rightleftharpoons HB^++OH^-$; and the $K_b$ of base, B, is defined as:

$$K_b = \frac{[HB^+][OH^-]}{[B]}.$$

In some embodiments, the pH is selected from about 8 or above; about 9 or above; about 10 or above; about 11 or above; and about 12 or above. In other embodiments, the pH is selected from a pH of 7 to 13; 7 to 12; 7 to 11; 7 to 10; 7 to 9; 8 to 13; 8 to 12; 8 to 11; 8 to 10; 8 to 9; 9 to 12; 9 to 11; 9 to 10; 10 to 12; and 10 to 11.

In some embodiments, the pH of the cells can be raised by a chloralkali process. In some embodiments, the fermentation broth containing sodium chloride and the cells is subjected to electrolysis that results in the formation of sodium hydroxide, which raises the pH of the cells. In some embodiments, the fermentation broth includes calcium chloride or potassium chloride instead of, or in addition to, sodium chloride, and electrolysis results in the formation of calcium hydroxide or potassium hydroxide, respectively, thereby raising the pH of the cell.

In some embodiments, the cells are lysed by lowering the pH of the cells. In some embodiments, the pH is lowered by adding an acid. The acids include, but are not limited to, sulfuric; phosphoric; hydrochloric; hydrobromic; hydroiodic; hypochlorous; chlorous; chloric; perchloric; fluorosulfuric; nitric; fluoroantimonic; fluoroboric; hexafluorophosphoric; chromic; boric; acetic; citric; formic; and combinations thereof. In some embodiments, the pH is selected from about 7 or below; about 6.5 or below; about 6 or below; about 5.5 or below; about 5 or below; about 4.5 or below; about 4 or below; about 3.5 or below; about 3 or below; about 2.5 or below; about 2 or below; about 1.5 or below; about 1 or below; and about 0.5 or below. In other embodiments, the pH is selected from about 0.5 to about 7; about 0.5 to about 6.5; about 0.5 to about 6; about 0.5 to about 5.5; about 0.5 to about 5; about 0.5 to about 4.5; about 0.5 to about 4; about 0.5 to about 3.5; about 0.5 to about 3; about 0.5 to about 2.5; about 0.5 to about 2; about 0.5 to about 1.5; about 0.5 to about 1; about 1 to about 7; about 1 to about 6.5; about 1 to about 6; about 1 to about 5.5; about 1 to about 5; about 1 to about 4.5; about 1 to about 4; about 1 to about 3.5; about 1 to about 3; about 1 to about 2.5; about 1 to about 2; about 1 to about 1.5; about 1.5 to about 7; about 1.5 to about 6.5; about 1.5 to about 6; about 1.5 to about 5.5; about 1.5 to about 5; about 1.5 to about 4.5; about 1.5 to about 4; about 1.5 to about 3.5; about 1.5 to about 3; about 1.5 to about 2.5; about 1.5 to about 2; about 2 to about 7; about 2 to about 6.5; about 2 to about 6; about 2 to about 5.5; about 2 to about 5; about 2 to about 4.5; about 2 to about 4; about 2 to about 3.5; about 2 to about 3; about 2 to about 2.5; about 2.5 to about 7; about 2.5 to about 6.5; about 2.5 to about 6; about 2.5 to about 5.5; about 2.5 to about 5; about 2.5 to about 4.5; about 2.5 to about 4; about 2.5 to about 3.5; about 2.5 to about 3; about 3 to about 7; about 3 to about 6.5; about 3 to about 6; about 3 to about 5.5; about 3 to about 5; about 3 to about 4.5; about 3 to about 4; about 3 to about 3.5; about 3.5 to about 7; about 3.5 to about 6.5; about 3.5 to about 6; about 3.5 to about 5.5; about 3.5 to about 5; about 3.5 to about 4.5; about 3.5 to about 4; about 4 to about 7; about 4 to about 6.5; about 4 to about 6; about 4 to about 5.5; about 4 to about 5; about 4 to about 4.5; about 4.5 to about 7; about 4.5 to about 6.5; about 4.5 to about 6; about 4.5 to about 5.5; about 4.5 to about 5; about 5 to about 7; about 5 to about 6.5; about 5 to about 6; about 5 to about 5.5; about 5.5 to about 7; about 5.5 to about 6.5; about 5.5 to about 6; about 6 to about 7; about 6 to about 6.5; and about 6.5 to about 7.

In some embodiments, an acid is added in an amount of about 2% to about 10%, about 2% to about 9%, about 2% to about 8%, about 2% to about 7%, about 2% to about 6%, about 3% to about 6%, about 4% to about 6%, about 5% to about 6%, about 2% to about 5%, about 2% to about 4%, about 2% to about 3%, about 3% to about 5%, about 3% to about 4%, or about 4% to about 5% by weight (or volume) of the cell broth to lower the pH.

Enzymatic treatment refers to contacting the cells with one or more enzymes. Enzymes include, but are not limited to, proteases, cellulases, hemicellulases, chitinases, pectinases, and combinations thereof. Non-limiting examples of proteases include serine proteases, theronine proteases, cysteine proteases, aspartate proteases, metalloproteases, glutamic acid proteases, alacase, and combinations thereof. Non-limiting examples of cellulases include sucrase, maltase, lactase, alpha-glucosidase, beta-glucosidase, amylase, lysozyme, neuraminidase, galactosidase, alpha-mannosidase, glucuronidase, hyaluronidase, pullulanase, glucocerebrosidase, galactosylceramidase, acetylgalactosaminidase, fucosidase, hexosaminidase, iduronidase, maltase-glucoamylase, and combinations thereof. A non-limiting example of a chitinase includes chitotriosidase. Non-limiting examples of pectinases include pectolyase, pectozyme, polygalacturonase, and combinations thereof. In some embodiments, some enzymes are activated by heating. In some embodiments, lysis does not include the use of enzymes.

As used herein, a "lysed cell composition" refers to a composition comprising one or more lysed cells, including cell debris and other contents of the cell, in combination with microbial oil (from the lysed cells), and optionally, broth that contains liquid (e.g., water), nutrients, and microbial cells. In some embodiments, a microbial cell is contained in a fermentation broth or media comprising water. In some embodiments, a lysed cell composition refers to a composition comprising one or more lysed cells, cell debris, microbial oil, the natural contents of the cell, and aqueous components from a fermentation broth. In one embodiment, the lysed cell composition comprises liquid, cell debris, and microbial oil. In some embodiments, a lysed cell composition is in the form of an oil-in-water emulsion comprising a mixture of a continuous aqueous phase and a dispersed oil phase. In some embodiments, a dispersed oil phase is present in a concentration of about 1% to about 60%; about 1% to about 50%; about 1% to about 40%; about 1% to about 30%; about 1% to about 20%; about 5% to about 60%; about 5% to about 50%; about 5% to about 40%; about 5% to about 30%; about 5% to about 20%; about 10% to about 60%; about 10% to about 50%; about 10% to about 40%; about 20% to about 60%; 20% to 50%, 20% to about 40%; about 30% to about 60%; about 30% to about 50%; or about 40% to about 60% by weight (or volume) of an emulsified lysed cell composition.

In some embodiments, lysing microbial cells results in the formation of an emulsion from endogenous materials in the cell or cell biomass including, but not limited to, proteins, phospholipids, carbohydrates, and combinations thereof. While not being bound to any particular theory, it is believed the processes of the present invention break-up or demulsify an emulsified lysed cell composition, allowing the microbial oil to be separated from the lysed cell composition. The terms "emulsion" and "emulsified" refers to a mixture of two or more immiscible phases or layers wherein one phase or layer is dispersed in another phase or layer. The terms "break," "break-up," "demulsify," "demulsification," "demulsifying," and "breaking" refer to a process of separating immiscible phases or layers of an emulsion. For example, demulsifying or breaking an emulsified lysed cell composition refers to a process by which an emulsified lysed cell composition changes from an emulsion having one or more phases or layers to a composition having two or more phases or layers. For example, in some embodiments, a process of the present invention breaks an emulsified lysed cell composition from a single-phase to two or more phases. In some embodiments, the two or more phases include an oil phase and an aqueous phase. In some embodiments, a process of the present invention breaks an emulsified lysed cell composition into at least three phases. In some embodiments, the three phases are selected from an oil phase, an aqueous phase, and a solid phase. In some embodiments, the phases are selected from an oil phase, an emulsion phase, an aqueous phase, and a solid phase.

In some embodiments, the process comprises demulsifying the lysed cell composition by lowering the pH of the lysed cell composition. In some embodiments, the pH is lowered by adding an acid. The acids include, but are not limited to, sulfuric; phosphoric; hydrochloric; hydrobromic; hydroiodic; hypochlorous; chlorous; chloric; perchloric; fluorosulfuric; nitric; fluoroantimonic; fluoroboric; hexafluorophosphoric; chromic; boric; acetic; citric; formic; and combinations thereof. In some embodiments, the pH is selected from 7 or less; about 6.5 or less; about 6 or less; about 5.5 or less; about 5 or less; about 4.5 or less; about 4 or less; about 3.5 or less; about 3 or less; about 2.5 or less; about 2 or less; about 1.5 or less; about 1 or less; and about 0.5 or less. In some embodiments, the process comprises lowering the pH of the lysed cell composition to about 6 or less. In other embodiments, the pH is selected from about 0.5 to about 7; about 0.5 to about 6.5; about 0.5 to about 6; about 0.5 to about 5.5; about 0.5 to about 5; about 0.5 to about 4.5; about 0.5 to about 4; about 0.5 to about 3.5; about 0.5 to about 3; about 0.5 to about 2.5; about 0.5 to about 2; about 0.5 to about 1.5; about 0.5 to about 1; about 1 to about 7; about 1 to about 6.5; about 1 to about 6; about 1 to about 5.5; about 1 to about 5; about 1 to about 4.5; about 1 to about 4; about 1 to about 3.5; about 1 to about 3; about 1 to about 2.5; about 1 to about 2; about 1 to about 1.5; about 1.5 to about 7; about 1.5 to about 6.5; about 1.5 to about 6; about 1.5 to about 5.5; about 1.5 to about 5; about 1.5 to about 4.5; about 1.5 to about 4; about 1.5 to about 3.5; about 1.5 to about 3; about 1.5 to about 2.5; about 1.5 to about 2; about 2 to about 7; about 2 to about 6.5; about 2 to about 6; about 2 to about 5.5; about 2 to about 5; about 2 to about 4.5; about 2 to about 4, about 2 to about 3.5; about 2 to about 3; about 2 to about 2.5; about 2.5 to about 7; about 2.5 to about 6.5; about 2.5 to about 6; about 2.5 to about 5.5; about 2.5 to about 5; about 2.5 to about 4.5; about 2.5 to about 4; about 2.5 to about 3.5; about 2.5 to about 3; about 3 to about 7; about 3 to about 6.5; about 3 to about 6; about 3 to about 5.5; about 3 to about 5; about 3 to about 4.5; about 3 to about 4; about 3 to about 3.5; about 3.5 to about 7; about 3.5 to about 6.5; about 3.5 to about 6; about 3.5 to about 5.5; about 3.5 to about 5; about 3.5 to about 4.5; about 3.5 to about 4; about 4 to about 7; about 4 to about 6.5; about 4 to about 6; about 4 to about 5.5; about 4 to about 5; about 4 to about 4.5; about 4.5 to about 7; about 4.5 to about 6.5; about 4.5 to about 6; about 4.5 to about 5.5; about 4.5 to about 5; about 5 to about 7; about 5 to about 6.5; about 5 to about 6; about 5 to about 5.5; about 5.5 to about 7; about 5.5 to about 6.5; about 5.5 to about 6; about 6 to about 7; about 6 to about 6.5; and about 6.5 to about 7. In some embodiments, the process comprises lowering the pH of the lysed cell composition to from about 0.5 to about 6.

In some embodiments, the process comprises demulsifying the lysed cell composition by adding an acid in an amount of from about 0.5% to about 20%, about 0.5% to about 15%, about 0.5% to about 10%, about 0.5% to about 9%, about 0.5% to about 8%, about 0.5% to about 7%, about 0.5% to about 6%, about 0.5% to about 5%, about 0.5% to about 4%, about 0.5% to about 3%, about 0.5% to about 2%, and about 0.5% to about 1%, by weight (or volume) of the cell broth or lysed cell composition. In one embodiment, the process comprises demulsifying the lysed cell composition by adding an acid in an amount of from about 0.5% to about 20%, by weight, lysed cell composition.

In some embodiments, the process further comprises heating prior to, during, or after lysing the cells. In some embodiments, the process comprises heating the lysed cell composition and/or cells to at least 10° C., at least 20° C., at least 25° C., at least 30° C., at least 35° C., at least 40° C., at least 45° C., at least 50° C., at least 55° C., at least 60° C., at least 65° C., at least 70° C., at least 75° C., at least 80° C., at least 85° C., at least 90° C., at least 95° C., or at least 100° C. In other embodiments, the process comprises heating the lysed cell composition and/or cells to from about 10° C. to about 100° C., about 10° C. to about 90° C., about 10° C. to about 80° C., about 10° C. to about 70° C., about 20° C. to about 100° C., about 20° C. to about 90° C., about 20° C. to about 80° C., about 20° C. to about 70° C., about 30° C. to about 100° C., about 30° C. to about 90° C., about 30° C. to about 80° C., about 30° C. to about 70° C., about 40° C. to about 100° C., about 40° C. to about 90° C., about 40° C. to about 80° C., about 50° C. to about 100° C., about 50° C. to about 90° C., about 50° C. to about 80° C., about 50° C. to about 70° C., about 60° C. to about 100° C., about 60° C. to about 90° C., about 60° C. to about 80° C., about 70° C. to about 100° C., about 70° C. to about 90° C., about 80° C. to about 100° C., about 80° C. to about 90° C., or about 90° C. to about 100° C. In further embodiments, the process comprises heating the lysed cell composition from about 70° C. to about 100° C., about 70° C. to about 90° C., about 80° C. to about 100° C., about 80° C. to about 90° C., or about 90° C. to about 100° C. In yet further embodiments, the process comprises heating the lysed cell composition to at least 70° C., at least 75° C., at least 80° C., at least 85° C., at least 90° C., at least 95° C., or at least 100° C. In still further embodiments, the process further comprises heating the lysed cell composition to at least 70° C. In yet another embodiment, the process further comprises heating the lysed cell composition to from about 70° C. to about 100° C.

In some embodiments, the process further comprises heating the lysed cell composition until the lysed cell composition comprises a mean particle size selected from 5 microns to 25 microns; 5 microns to 20 microns; 5 microns to 15 microns; 10 microns to 25 microns; 10 microns to 20 microns; 10 microns to 15 microns; 15 microns to 25 microns; 15 microns to 20 microns; and 20 microns to 25 microns. In a further embodiment, the mean particle size of the lysed cell composition is selected from 25 microns or less, 20 microns or less, 15 microns or less, 10 microns or less, and 5 microns or less. In a further embodiment, the mean particle size of the lysed cell composition is 25 microns or less. In some embodiments, the mean particle size can be measured using, e.g., a Beckman Coulter LS 13 320 particle size analyzer (Beckman Coulter, Brea, Calif.). In some embodiments, the mean particle size can be measured using, e.g., a Malvern MS2000 particle size analyzer (Malvern Instruments Ltd., Worcestershire, United Kingdom). In some embodiments, the lysed cell composition is heated for a sufficient period of time to demulsify the lysed cell composition.

In some embodiments, cells and/or a lysed cell composition can be heated in a closed system or in a system with an evaporator. In some embodiments, cells and/or lysed cell composition can be heated in a system with an evaporator such that a portion of the water present in the cells and/or the lysed cell composition is removed by evaporation. In some embodiments, a process comprises heating cells and/or a lysed cell composition in a system with an evaporator to remove up to 1%, 5%, 10%, 15%, 20%, 25%, 30%, 35%, 40%, 45% or 50% by weight (or volume) of water present in the cells and/or the lysed cell composition. In some embodiments, a process comprises heating cells and/or a lysed cell composition in a system with an evaporator to remove 1% to 50%, 1% to 45%, 1% to 40%, 1% to 35%, 1% to 30%, 1% to 25%, 1% to 20%, 1% to 15%, 1% to 10%, 1% to 5%, 5% to 50%, 5% to 45%, 5% to 40%, 5% to 35%, 5% to 30%, 5% to 25%, 5% to 20%, 5% to 15%, 5% to 10%, 10% to 50%, 10% to 45%, 10% to 40%, 10% to 35%, 10% to 30%, 10% to 25%, 10% to 20%, 10% to 15%, 15% to 50%, 15% to 45%, 15% to 40%, 15% to 35%, 15% to 30%, 15% to 25%, 15% to 20%, 20% to 50%, 20% to 45%, 20% to 40%, 20% to 35%, 20% to 30%, 20% to 25%, 25% to 50%, 25% to 45%, 25% to 40%, 25% to 35%, 25% to 30%, 30% to 50%, 30% to 45%, 30% to 40%, 30% to 35%, 35% to 50%, 35% to 45%, 35% to 40%, 40% to 50%, 40% to 45%, or 45% to 50% by weight (or volume) of water.

In some embodiments, the process further comprises adding an emulsifier to a lysed cell composition. In some embodiments, the emulsifier is a detergent. In some embodiments, the emulsifier is a surfactant. In some embodiments, the emulsifier is added prior to, during, or after lysis. In one embodiment, the emulsifier is added after lysis. In some embodiments, the emulsifier is added to the lysed cell composition. As used herein, the term "emulsifier" refers to a substance that stabilizes an emulsion. Emulsifiers are selected from ionic emulsifiers, nonionic emulsifiers, and combinations thereof. In some embodiments, the emulsifier is an ionic emulsifier.

In some embodiments, the ionic emulsifier is selected from anionic emulsifiers, cationic emulsifiers, and combinations thereof. In some embodiments, the anionic emulsifiers can be anionic sulfate emulsifiers, such as, for example, alkyl sulfates (e.g., ammonium lauryl sulfate, sodium lauryl sulfate (SLS)/sodium dodecyl sulfate (SDS), and combinations thereof), alkyl ether sulfates (e.g., sodium laureth sulfate/sodium lauryl ether sulfate, sodium myreth sulfate, and combinations thereof), and combinations thereof; anionic sulfonate emulsifiers, such as, for example, docusates (e.g., dioctyl sodium sulfosuccinate, sulfonate fluorosurfactants (e.g., perfluorooctanesulfonate and perfluorobutanesulfonate), alkyl benzene sulfonates, and combinations thereof); anionic phosphate emulsifiers (e.g., alkyl aryl ether phosphate, alkyl ether phosphate, and combinations thereof); anionic carboxylate emulsifiers (e.g., alkyl carboxylates, (e.g., sodium stearate, sodium lauroyl sarcosinate. carboxylate fluorosurfactants (e.g., pefluorononanoate, perfluorooctanoate, and combinations thereof), and combinations thereof; and combinations thereof. In some embodiments, the emulsifier is an anionic emulsifier. In one embodiment, the anionic emulsifier is selected from an anionic sulfate emulsifier, an anionic sulfonate emulsifier, an anionic phosphate emulsifier, an anionic carboxylate emulsifier, and combinations thereof. In another embodiment, an anionic emulsifier is an anionic sulfate emulsifier. In a still further embodiment, an anionic sulfate emulsifier is selected from ammonium lauryl sulfate, sodium dodecyl sulfate, sodium laureth sulfate, sodium lauryl ether sulfate, sodium myreth sulfate, and combinations thereof. In yet an even further embodiment, an anionic sulfate emulsifier is sodium dodecyl sulfate.

In some embodiments, the cationic emulsifier can be a pH-dependent primary amine; a pH-dependent secondary amine; a pH-dependent tertiary amine; octenidine dihydrochloride; a permanently charged quaternary ammonium cation (e.g., alkyltrimethylammonium salts (e.g., cetyl trimethylammonium bromide (CTAB)/hexadecyl trimethyl ammonium bromide, cetyl trimethylammonium chloride (CTAC), and combinations thereof), cetylpyridinium chloride (CPC), benzalkonium chloride (BAC), benzethonium chloride (BZT), 5-bromo-5-nitro-1,3-dioxane, dimethyldioctadecylammonium chloride, dioctadecyldimethylammonium bromide (DODAB), and combinations thereof); and combinations thereof.

In some embodiments, the molecular weight of the emulsifier is selected from 500 g/mole or less, 450 g/mole or less, 400 g/mole or less, 350 g/mole or less, and 300 g/mole or less. In a further embodiment, the molecular weight of the emulsifier is selected from 250 g/mole to 500 g/mole, 250 g/mole to 450 g/mole, 250 g/mole to 400 g/mole, 250 g/mole to 350 g/mole, 250 g/mole to 300 g/mole, 300 g/mole to 500 g/mole, 300 g/mole to 450 g/mole, 300 g/mole to 400 g/mole, 300 g/mole to 350 g/mole, 350 g/mole to 500 g/mole, 350 g/mole to 450 g/mole, 350 g/mole to 400 g/mole, 400 g/mole to 500 g/mole, 400 g/mole to 450 g/mole, and 450 g/mole to 500 g/mole. For example, the molecular weight of SDS is 288 g/mole, and the molecular weight of CTAB is 364 g/mole. In yet a further embodiment, the molecular weight of the emulsifier is selected from 250 g/mole to 450 g/mole, 250 g/mole to 400 g/mole, 250 g/mole to 350 g/mole, and 250 g/mole to 300 g/mole.

In some embodiments, an emulsifier is added as a powder. In some embodiments, an emulsifier is added in a solution having a concentration of emulsifier in an amount of 5% to 50%, 5% to 45%, 5% to 40%, 5% to 35%, 5% to 30%, 10% to 50%, 10% to 45%, 10% to 40%, 10% to 35%, 10% to 30%, 15% to 50%, 15% to 45%, 15% to 40%, 15% to 35%, 15% to 30%, 20% to 50%, 20% to 45%, 20% to 40%, 20% to 35%, 20% to 30%, 25% to 50%, 25% to 45%, 25% to 40%, 25% to 35%, 25% to 30%, 30% to 50%, 30% to 45%, 30% to 40%, and 30% to 35%.

In some embodiments, an emulsifier (e.g., in powder form or in solution) is added in an amount selected from 0.2% to 10%, 0.2% to 9.5%, 0.2% to 9%, 0.2% to 8.5%, 0.2% to 8%, 0.2% to 7.5%, 0.2% to 7%, 0.2% to 6.5%, 0.2% to 6%, 0.2% to 5.5%, 0.2% to 5%, 0.2% to 4.5%, 0.2% to 4%, 0.2% to 3.5%, 0.2% to 3%, 0.2% to 2.5%, 0.2% to 2%, 0.2% to 1.5%, 0.2% to 1%, 0.2% to 0.5%, 0.5% to 10%, 0.5% to 9.5%, 0.5% to 9%, 0.5% to 8.5%, 0.5% to 8%, 0.5% to 7.5%, 0.5% to 7%, 0.5% to 6.5%, 0.5% to 6%, 0.5% to 5.5%, 0.5% to 5%, 0.5% to 4.5%, 0.5% to 4%, 0.5% to 3.5%, 0.5% to 3%, 0.5% to 2.5%, 0.5% to 2%, 0.5% to 1.5%, 0.5% to 1%, 1% to 10%, 1% to 9.5%, 1% to 9%, 1% to 8.5%, 1% to 8%, 1% to 7.5%, 1% to 7%, 1% to 6.5%, 1% to 6%, 1% to 5.5%, 1% to 5%, 1% to 4.5%, 1% to 4%, 1% to 3.5%, 1% to 3%, 1% to 2.5%, 1% to 2%, 1% to 1.5%, 1.5% to 10%, 1.5% to 9.5%, 1.5% to 9%, 1.5% to 8.5%, 1.5% to 8%, 1.5% to 7.5%, 1.5% to 7%, 1.5% to 6.5%, 1.5% to 6%, 1.5% to 5.5%, 1.5% to 5%, 1.5% to 4.5%, 1.5% to 4%, 1.5% to 3.5%, 1.5% to 3%, 1.5% to 2.5%, 1.5% to 2%, 2% to 10%, 2% to 9.5%, 2% to 9%, 2% to 8.5%, 2% to 8%, 2% to 7.5%, 2% to 7%, 2% to 6.5%, 2% to 6%, 2% to 5.5%, 2% to 5%, 2% to 4.5%, 2% to 4%, 2% to 3.5%, 2% to 3%, 2% to 2.5%, 2.5% to 10%, 2.5% to 9.5%, 2.5% to 9%, 2.5% to 8.5%, 2.5% to 8%, 2.5% to 7.5%, 2.5% to 7%, 2.5% to 6.5%, 2.5% to 6%, 2.5% to 5.5%, 2.5% to 5%, 2.5% to 4.5%, 2.5% to 4%, 2.5% to 3.5%, 2.5% to 3%, 3% to 10%, 3% to 9.5%, 3% to 9%, 3% to 8.5%, 3% to 8%, 3% to 7.5%, 3% to 7%, 3% to 6.5%, 3% to 6%, 3% to 5.5%, 3% to 5%, 3% to 4.5%, 3% to 4%, and 3% to 3.5% by weight (or volume) of the fermentation broth or lysed cell composition. In another embodiment, an emulsifier (e.g., in powder form or in solution) is added in an amount selected from 0.2% to 5%, 0.5% to 5%, 1% to 5%, 1.5% to 5%, 2% to 5%, 2.5% to 5%, and 3% to 5% by weight (or volume) of the fermentation broth or lysed cell composition. In yet a further embodiment, an emulsifier is added in an amount of from 0.2% to 10% by weight of the lysed cell composition.

In some embodiments, the emulsifier decreases the interfacial tension (i.e., surface tension) of the fermentation broth or lysed cell composition. As used herein, the term "interfacial tension" or "surface tension" refers to the force which acts on an imaginary line one meter in length at the interface between two phases. In some embodiments, the interfacial tension of the emulsion formed by the emulsifier is lower than an emulsion formed by the endogenous materials. In some embodiments, the interfacial tension can be measured in dynes/cm.

In some embodiments, the emulsifier increases an absolute value of the zeta potential of the fermentation broth or lysed cell composition (i.e., increases a positive zeta potential or decreases a negative zeta potential). In some embodiments, the addition of an anionic emulsifier can result in a downward shift in the zeta potential of the fermentation broth or lysed cell composition (e.g., decreases a positive zeta potential or increases a negative zeta potential). In some embodiments, the addition of a cationic emulsifier can result in an upward shift in zeta potential of the fermentation broth or lysed cell composition (e.g., increases a positive zeta potential or increases a negative zeta potential). As used herein, the term "zeta potential" refers to the electrokinetic potential between particles in the emulsion. In some embodiments, the zeta potential can be measured in mV. In some embodiments, the absolute value of the zeta potential of the emulsion formed by the emulsifier is higher than an emulsion formed by the endogenous materials.

In some embodiments, the addition of an ionic emulsifier creates an oil-in-water emulsion. In some embodiments, the oil-in-water emulsion includes, but is not limited to, oil, water, and an ionic emulsifier.

In some embodiments, the process further comprises adding a salt to the lysed cell composition. The term "salt" refers to an ionic compound formed by replacing a hydrogen ion from an acid with a metal (e.g., an alkali metal, an alkali earth metal, and a transition metal) or a positively charged compound (e.g., $NH_4^+$). In some embodiments, the salt can be an alkali metal salt, alkali earth metal salts, sulfate salts, or combinations thereof. Negatively charged ionic species present in a salt include, but are not limited to, halides, sulfate, bisulfate, sulfite, phosphate, hydrogen phosphate, dihydrogen phosphate, carbonate, bicarbonate, and combinations thereof. In some embodiments, a salt is selected from sodium chloride, sodium sulfate, sodium carbonate, calcium chloride, potassium sulfate, magnesium sulfate, monosodium glutamate, ammonium sulfate, potassium chloride, iron chloride, iron sulfate, aluminum sulfate, ammonium acetate, and combinations thereof. In some embodiments, a salt does not include NaOH. A salt can be added as a solid (e.g., in crystalline, amorphous, pelletized, and/or granular form), and/or as a solution (e.g., a dilute solution, a saturated solution, or a super-saturated solution) containing, for example, water.

In some embodiments, the salt is added in an amount of 5 g/l to 25 g/l, 5 g/l to 10 g/l, 10 g/l to 15 g/l, 15 g/l to 20 g/l, 20 g/l to 25 g/l, or 10 g/l to 20 g/l.

In other embodiments, a salt is added to the lysed cell composition in an amount of 20% or less, 15% or less, 10% or less, 7.5% or less, 5% or less, or 2% or less by weight (or volume), of the lysed cell composition. In some embodiments, a salt is added to the lysed cell composition in an amount of from about 0.05% to about 20%, about 0.1% to about 20%, about 0.1% to about 15%, about 0.1% to about 10%, about 0.5% to about 20%, about 0.5% to about 15%, about 0.5% to about 10%, about 0.5% to about 5%, about 0.5% to about 4%, about 0.5% to about 3%, about 0.5% to about 2.5%, about 0.5% to about 2%, about 0.5% to about 1.5%, about 0.5% to about 1%, about 1% to about 20%, about 1% to about 15%, about 1% to about 10%, about 1% to about 5%, about 1% to about 4%, 1% to about 3%, about 1% to about 2.5%, about 1% to about 2%, about 1% to about 1.5%, about 1.5% to about 5%, about 1.5% to about 4%, about 1.5% to about 3%, about 1.5% to about 2.5%, about 1.5% to about 2%, about 2% to 20%, about 2% to about 15%, about 2% to about 10%, about 2% to about 5%, about 2% to about 4%, about 2% to about 3%, about 2% to about 2.5%, about 2.5% to about 5%, about 2.5% to about 4%, about 2.5% to about 3%, about 3% to about 5%, about 3% to about 4%, about 4% to about 5%, about 5% to about 20%, about 5% to about 15%, about 5% to about 10%, about 10% to about 20%, about 10% to about 15%, or about 15% to about 20%, by weight (or volume), lysed cell composition (e.g., a total broth weight (or volume)). For example, when a lysed cell composition weighs 1,000 kg, salt that is added in an amount of 0.5% to 20%, by weight (or volume), requires the addition of 5 kg to 200 kg salt to the lysed cell composition. In some embodiments, a salt is added to the lysed cell composition in an amount of from about 0.05% to about 20%, about 0.1% to about 20% by weight (or volume), about 0.5% to about 15% by weight (or volume), or about 2% to about 10% by weight (or volume) of the lysed cell composition.

In some embodiments, the process further comprises agitating (i) prior to, during, or after lysing the cells; (i) prior to, during, or after demulsifying the lysed cell composition; or a combination thereof. The terms "agitating" and "agitation" refer to a process of affecting motion in the cells and/or the lysed cell composition through an application of force. In some embodiments, the process comprises agitating the cells and/or the lysed cell composition by stirring, mixing, blending, shaking, vibrating, or a combination thereof.

In some embodiments, the agitator is a dispersion style agitator that disperses a base and/or salt in the cell composition or the lysed cell composition. In some embodiments, the agitator has a heating plate. In some embodiments, the agitator has a mantle for stirring. In some embodiments, an agitator has one or more impellers. As used herein, "impeller" refers to a device arranged to impart motion to a cell composition or a lysed cell composition when rotated. Impellers suitable for use with the present invention include straight blade impellers, Rushton blade impellers, axial flow impellers, radial flow impellers, concave blade disc impellers, high-efficiency impellers, propellers, paddles, turbines, and combinations thereof.

In some embodiments, the process of the invention comprises agitating the cells and/or the lysed cell composition at 0.1 hp/1,000 gal to 10 hp/1,000 gal, 0.5 hp/1,000 gal to 8 hp/1,000 gal, 1 hp/1,000 gal to 6 hp/1,000 gal, or 2 hp/1,000 gal to 5 hp/1,000 gal of cells or composition, respectively. In some embodiments, the process comprises agitating the cells and/or lysed cell composition at 0.1 hp/1000 gal to 10 hp/1000 gal of cells or composition, respectively.

In some embodiments the invention comprises agitating at 10 rpm or below, 20 rpm or below, 50 rpm or below, 100 rpm or below, 150 rpm or below, 200 rpm or below, 250 rpm or below, 300 rpm or below, 350 rpm or below, 400 rpm or below, 10 rpm to 400 rpm, 10 rpm to 350 rpm, 10 rpm to 300 rpm, 10 rpm to 250 rpm, 10 rpm to 200 rpm, 10 rpm to 150 rpm, 10 rpm to 100 rpm, 10 rpm to 50 rpm, 10 rpm to 20 rpm, 20 rpm to 400 rpm, 20 rpm to 350 rpm, 20 rpm to 300 rpm, 20 rpm to 250 rpm, 20 rpm to 200 rpm, 20 rpm to 150 rpm, 20 rpm to 100 rpm, 20 rpm to 50 rpm, 50 rpm to 400 rpm, 50 rpm to 350 rpm, 50 rpm to 300 rpm, 50 rpm to 250 rpm, 50 rpm to 200 rpm, 50 rpm to 150 rpm, 50 rpm to 100 rpm, 100 rpm to 400 rpm, 100 rpm to 350 rpm, 100 rpm to 300 rpm, 100 rpm to 250 rpm, 100 rpm to 200 rpm, 100 rpm to 150 rpm, 150 rpm to 400 rpm, 150 rpm to 350 rpm, 150 rpm to 300 rpm, 150 rpm to 250 rpm, 150 rpm to 200 rpm, 200 rpm to 400 rpm, 200 rpm to 350 rpm, 200 rpm to 300 rpm, 200 rpm to 250 rpm, 250 rpm to 400 rpm, 250 rpm to 350 rpm, 250 rpm to 300 rpm, 300 rpm to 400 rpm, 300 rpm to 350 rpm, or 350 rpm to 400 rpm. In some embodiments, the agitating occurs at a rate of 350 rpm or less.

In some embodiments, the process includes agitating cells and/or a lysed cell composition using an agitator having an impeller tip speed of 90 ft/min to 1,200 ft/min, 200 ft/min to 1,000 ft/min, 300 ft/min to 800 ft/min, 400 ft/min to 700 ft/min, or 500 ft/min to 600 ft/min. In some embodiments, the process comprises agitating with an agitator having an impeller tip speed of 200 ft/min to 1000 ft/min.

In some embodiments, a process includes agitating cells and/or a lysed cell composition using an agitator having an impeller tip speed of 5 cm/sec to 900 cm/sec, 5 cm/sec to 750 cm/sec, 5 cm/sec to 500 cm/sec, 5 cm/sec to 350 cm/sec, 5 cm/sec to 300 cm/sec, 5 cm/sec to 250 cm/sec, 5 cm/sec to 200 cm/sec, 5 cm/sec to 150 cm/sec, 5 cm/sec to 100 cm/sec, 5 cm/sec to 50 cm/sec, 5 cm/sec to 25 cm/sec, 25 cm/sec to 900 cm/sec, 25 cm/sec to 750 cm/sec, 25 cm/sec to 500 cm/sec, 25 cm/sec to 350 cm/sec, 25 cm/sec to 300 cm/sec, 25 cm/sec to 250 cm/sec, 25 cm/sec to 200 cm/sec, 25 cm/sec to 150 cm/sec, 25 cm/sec to 100 cm/sec, 25 cm/sec to 50 cm/sec, 50 cm/sec to 900 cm/sec, 50 cm/sec to 750 cm/sec, 50 cm/sec to 500 cm/sec, 50 cm/sec to 350 cm/sec, 50 cm/sec to 300 cm/sec, 50 cm/sec to 250 cm/sec, 50 cm/sec to 200 cm/sec, 50 cm/sec to 150 cm/sec, 50 cm/sec to 100 cm/sec, 100 cm/sec to 900 cm/sec, 100 cm/sec to 750 cm/sec, 100 cm/sec to 500 cm/sec, 100 cm/sec to 350 cm/sec, 100 cm/sec to 300 cm/sec, 100 cm/sec to 250 cm/sec, 100 cm/sec to 200 cm/sec, 100 cm/sec to 150 cm/sec, 150 cm/sec to 900 cm/sec, 150 cm/sec to 750 cm/sec, 150 cm/sec to 500 cm/sec, 150 cm/sec to 350 cm/sec, 150 cm/sec to 300 cm/sec, 150 cm/sec to 250 cm/sec, 150 cm/sec to 200 cm/sec, 200 cm/sec to 900 cm/sec, 200 cm/sec to 750 cm/sec, 200 cm/sec to 500 cm/sec, 200 cm/sec to 300 cm/sec, 200 cm/sec to 250 cm/sec, 250 cm/sec to 900 cm/sec, 250 cm/sec to 750 cm/sec, 250 cm/sec to 500 cm/sec, 250 cm/sec to 350 cm/sec, 250 cm/sec to 300 cm/sec, 300 cm/sec to 900 cm/sec, 300 cm/sec to 750 cm/sec, 300 cm/sec to 500 cm/sec, 300 cm/sec to 350 cm/sec, 350 cm/sec to 900 cm/sec, 350 cm/sec to 850 cm/sec, 350 cm/sec to 800 cm/sec, 350 cm/sec to 750 cm/sec, 350 cm/sec to 700 cm/sec, 350 cm/sec to 650 cm/sec, 350 cm/sec to 600 cm/sec, 350 cm/sec to 550 cm/sec, 350 cm/sec to 500 cm/sec, 350 cm/sec to 450 cm/sec, 350 cm/sec to 400 cm/sec, 400 cm/sec to 900 cm/sec, 400 cm/sec to 850 cm/sec, 400 cm/sec to 800 cm/sec, 400 cm/sec to 750 cm/sec, 400 cm/sec to 700 cm/sec, 400 cm/sec to 650 cm/sec, 400 cm/sec to 600 cm/sec, 400 cm/sec to 550 cm/sec, 400 cm/sec to 500 cm/sec, 400 cm/sec to 450 cm/sec, 450 cm/sec to 900 cm/sec, 450 cm/sec to 850 cm/sec, 450 cm/sec to 800 cm/sec, 450 cm/sec to 750 cm/sec, 450 cm/sec to 700 cm/sec, 450 cm/sec to 650 cm/sec, 450 cm/sec to 600 cm/sec, 450 cm/sec to 550 cm/sec, 450 cm/sec to 500 cm/sec, 500 cm/sec to 900 cm/sec, 500 cm/sec to 850 cm/sec, 500 cm/sec to 800 cm/sec, 500 cm/sec to 750 cm/sec, 500 cm/sec to 700 cm/sec, 500 cm/sec to 650 cm/sec, 500 cm/sec to 600 cm/sec, 500 cm/sec to 550 cm/sec, 550 cm/sec to 900 cm/sec, 550 cm/sec to 850 cm/sec, 550 cm/sec to 800 cm/sec, 550 cm/sec to 750 cm/sec, 550 cm/sec to 700 cm/sec, 550 cm/sec to 650 cm/sec, 550 cm/sec to 600 cm/sec, 600 cm/sec to 900 cm/sec, 600 cm/sec to 850 cm/sec, 600 cm/sec to 800 cm/sec, 600 cm/sec to 750 cm/sec, 600 cm/sec to 700 cm/sec, 600 cm/sec to 650 cm/sec, 650 cm/sec to 900 cm/sec, 650 cm/sec to 850 cm/sec, 650 cm/sec to 800 cm/sec, 650 cm/sec to 750 cm/sec, 650 cm/sec to 700 cm/sec, 700 cm/sec to 900 cm/sec, 700 cm/sec to 850 cm/sec, 700 cm/sec to 800 cm/sec, 700 cm/sec to 750 cm/sec, 750 cm/sec to 900 cm/sec, 750 cm/sec to 850 cm/sec, 750 cm/sec to 800 cm/sec, 800 cm/sec to 900 cm/sec, 800 cm/sec to 850 cm/sec, or 850 cm/sec to 900 cm/sec. The term "impeller tip speed" refers to the speed of the outer most portion of the impeller as it rotates around its central axis.

In some embodiments, the agitating (and optional additional steps as described herein) is performed in a container comprising an impeller, wherein a ratio of the impeller diameter to the container volume is 0.1 to 0.5, 0.1 to 0.4, 0.2 to 0.5, 0.2 to 0.4, 0.3 to 0.5, or 0.3 to 0.4.

In some embodiments, the agitating (and optional additional steps as described herein) is performed in a container comprising an impeller, wherein a ratio of the impeller diameter to the inner diameter of the container is at least 0.25, at least 0.34, at least 0.65, 0.25 to 0.65, 0.25 to 0.33, 0.3 to 0.6, 0.3 to 0.5, 0.3 to 0.4, 0.34 to 0.65, 0.34 to 0.6, 0.34 to 0.55, 0.37 to 0.55, 0.4 to 0.65, 0.4 to 0.6, 0.4 to 0.5, or 0.42 to 0.55.

In some embodiments, agitating comprises mixing cells and/or a lysed cell composition such that the cells and/or the lysed cell composition is placed under flow conditions described by a Reynolds number of 10 to 10,000, 1,000 to 10,000, 1,500 to 10,000, or 2,000 to 10,000. In some embodiments, a lysed cell emulsion during the agitating has a Reynolds number of 2,000 or more, 3,000 or more, or 5,000 or more, or 2,000 to 10,000, 3,000 to 10,000, or 5,000 to 10,000.

In some embodiments, the agitation vessels can have two impellers. In some embodiments, the impellers are Rushton blade impellers. In some embodiments, the impellers are separated from each other by a distance at least equal to a diameter of the smallest impeller. In some embodiments, the impellers are 30 inches to 40 inches, 33 inches to 37 inches, 33 inches, 34 inches, 35 inches, 36 inches or 37 inches from tip to tip. In some embodiments, the agitation vessels have a volume of at least 10,000 liters, at least 20,000 liters, at least 30,000 liters, at least 40,000 liters or at least 50,000 liters. In some embodiments, the agitation vessels have an inner diameter of 90 inches to 110 inches, 95 inches to 105 inches, 98 inches, 99 inches, 100 inches, 101 inches, or 102 inches. In some embodiments, a first impeller is located 15 inches to 20 inches, 16 inches to 19 inches, or 17 inches to 18 inches from a bottom of the agitation vessel and a second impeller is located 60 inches to 80 inches, 65 inches to 75 inches, 68 inches, 69 inches, 70 inches, 71 inches, 72 inches, 73 inches, 74 inches, or 75 inches above the first impeller. In some embodiments, a lysed cell composition is agitated at least 50 rpm, at least 60 rpm, or at least 70 rpm. In some embodiments, a lysed cell composition is agitated at 50 rpm to 70 rpm, 50 rpm to 60 rpm, or 60 rpm to 70 rpm.

In some embodiments, the process further comprises agitating the lysed cell composition. In some embodiments, the process of agitating a lysed cell composition demulsifies the lysed cell composition.

In some embodiments, the mean particle size of the oil droplets formed during demulsification is selected from 5 microns to 50 microns; 5 microns to 45 microns; 5 microns to 40 microns; 5 microns to 35 microns; 5 microns to 30 microns; 5 microns to 25 microns; 5 microns to 20 microns; 5 microns to 15 microns; 10 microns to 50 microns; 10 microns to 45 microns; 10 microns to 40 microns; 10 microns to 35 microns; 10 microns to 30 microns; 10 microns to 25 microns; 10 microns to 20 microns; 10 microns to 15 microns; 15 microns to 50 microns; 15 microns to 45 microns; 15 microns to 40 microns; 15 microns to 35 microns; 15 microns to 30 microns; 15 microns to 25 microns; 15 microns to 20 microns; 20 microns to 50 microns; 20 microns to 45 microns; 20 microns to 40 microns; 20 microns to 35 microns; 20 microns to 30 microns; 20 microns to 25 microns; 25 microns to 50 microns; 25 microns to 45 microns; 25 microns to 40 microns; 25 microns to 35 microns; 25 microns to 30 microns; 30 microns to 50 microns; 30 microns to 45 microns; 30 microns to 40 microns; 30 microns to 35 microns; 35 microns to 50 microns; 35 microns to 40 microns; 40 microns to 50 microns; 40 microns to 45 microns; and 45 microns to 50 microns. In a further embodiment, the mean particle size of the oil droplets formed during demulsification is selected from at least 10 microns, at least 15 microns, at least 20 microns, at least 25 microns, at least 30 microns, at least 35 microns, and at least 40 microns or above. In further embodiments, the mean particle size of the oil droplets formed during demulsification is selected from at least 10 microns, at least 15 microns, at least 20 microns, and at least 25 microns. In some embodiments, the mean particle size can be measured using, e.g., a Beckman Coulter LS 13 320 particle size analyzer (Beckman Coulter, Brea, Calif.). In some embodiments, the mean particle size can be measured using, e.g., a Malvern MS2000 particle size analyzer (Malvern Instruments Ltd., Worcestershire, United Kingdom).

In some embodiments, the lysed cell composition is subjected to one or more of an emulsifier, an acid, a salt, heat, and agitation to form a demulsified lysed cell composition.

In some embodiments, the process further comprises combining the lysing and demulsifying steps together to form a one-step lysing and demulsifying step.

In some embodiments, the process further comprises combining the lysing and demulsifying steps together to form a one-step lysing and demulsifying step that comprises raising the pH of the cells and the lysed cell composition. In some embodiments, the one-step lysing and demulsifying step comprises raising the pH of the cells and the lysed cell composition to about 8 or above. In some embodiments, the one-step lysing and demulsifying step comprises adding a base to raise the pH of the cells and the lysed cell composition. In some embodiments, the one-step lysing and demulsifying step comprises adding a base to raise the pH of the cells and the lysed cell composition to about 8 or above.

In some embodiments, the base that can be added to the one step lysing and demulsifying step is selected from a base already described hereinabove. In some embodiments, the pH of the cells and the lysed cell composition of the one-step lysing and demulsifying step can be raised to a pH selected from about 8 or above; about 9 or above; about 10 or above; about 11 or above; and about 12 or above. In other embodiments, the pH of the cells and the lysed cell composition of the one-step lysing and demulsifying step can be raised to a pH selected from 7 to 13; 7 to 12; 7 to 11; 7 to 10; 7 to 9; 8 to 13; 8 to 12; 8 to 11; 8 to 10; 8 to 9; 9 to 12; 9 to 11; 9 to 10; 10 to 12; and 10 to 11.

In some embodiments, the cells are lysed at a suitable pH to form a demulsified lysed cell composition. In some embodiments, a suitable pH is attained by adding a base as already described hereinabove. In some embodiments, a suitable pH is selected from 7 to 13; 7 to 12; 7 to 11; 7 to 10; 7 to 9; 8 to 13; 8 to 12; 8 to 11; 8 to 10; 8 to 9; 9 to 13; 9 to 12; 9 to 11; 9 to 10; 10 to 13; 10 to 12; and 10 to 11. In other embodiments, a suitable pH is selected from 10 to 13. In yet further embodiments, a suitable pH is selected from at least 10, at least 11, at least 12, and at least 13.

In some embodiments, a suitable pH is attained by adding a base in an amount selected from about 0.5% to about 20%, about 0.5% to about 15%, about 0.5% to about 10%, about 0.5% to about 9%, about 0.5% to about 8%, about 0.5% to about 7%, about 0.5% to about 6%, about 0.5% to about 5%, about 0.5% to about 4%, about 0.5% to about 3%, about 0.5% to about 2%, and about 0.5% to about 1%, by weight (or volume) of the cell broth or composition. In one embodiment, a suitable pH is attained by adding a base in an amount of from about 0.5% to about 20%, by weight broth.

In other embodiments, a suitable pH is attained by adding an acid as already described hereinabove. In some embodiments, a suitable pH is selected from 7 or less; about 6.5 or less; about 6 or less; about 5.5 or less; about 5 or less; about 4.5 or less; about 4 or less; about 3.5 or less; about 3 or less; about 2.5 or less; about 2 or less; about 1.5 or less; about 1 or less; and about 0.5 or less. In some embodiments, a suitable pH is selected from about 6 or less. In other embodiments, the pH is selected from about 0.5 to about 7; about 0.5 to about 6.5; about 0.5 to about 6; about 0.5 to about 5.5; about 0.5 to about 5; about 0.5 to about 4.5; about 0.5 to about 4; about 0.5 to about 3.5; about 0.5 to about 3; about 0.5 to about 2.5; about 0.5 to about 2; about 0.5 to about 1.5; about 0.5 to about 1; about 1 to about 7; about 1 to about 6.5; about 1 to about 6; about 1 to about 5.5; about 1 to about 5; about 1 to about 4.5; about 1 to about 4; about 1 to about 3.5; about 1 to about 3; about 1 to about 2.5; about 1 to about 2; about 1 to about 1.5; about 1.5 to about 7; about 1.5 to about 6.5; about 1.5 to about 6; about 1.5 to about 5.5; about 1.5 to about 5; about 1.5 to about 4.5; about 1.5 to about 4; about 1.5 to about 3.5; about 1.5 to about 3; about 1.5 to about 2.5; about 1.5 to about 2; about 2 to about 7; about 2 to about 6.5; about 2 to about 6; about 2 to about 5.5; about 2 to about 5; about 2 to about 4.5; about 2 to about 4, about 2 to about 3.5; about 2 to about 3; about 2 to about 2.5;

about 2.5 to about 7; about 2.5 to about 6.5; about 2.5 to about 6; about 2.5 to about 5.5; about 2.5 to about 5; about 2.5 to about 4.5; about 2.5 to about 4; about 2.5 to about 3.5; about 2.5 to about 3; about 3 to about 7; about 3 to about 6.5; about 3 to about 6; about 3 to about 5.5; about 3 to about 5; about 3 to about 4.5; about 3 to about 4; about 3 to about 3.5; about 3.5 to about 7; about 3.5 to about 6.5; about 3.5 to about 6; about 3.5 to about 5.5; about 3.5 to about 5; about 3.5 to about 4.5; about 3.5 to about 4; about 4 to about 7; about 4 to about 6.5; about 4 to about 6; about 4 to about 5.5; about 4 to about 5; about 4 to about 4.5; about 4.5 to about 7; about 4.5 to about 6.5; about 4.5 to about 6; about 4.5 to about 5.5; about 4.5 to about 5; about 5 to about 7; about 5 to about 6.5; about 5 to about 6; about 5 to about 5.5; about 5.5 to about 7; about 5.5 to about 6.5; about 5.5 to about 6; about 6 to about 7; about 6 to about 6.5; and about 6.5 to about 7. In some embodiments, a suitable pH is selected from about 0.5 to about 6.

In some embodiments, the process comprises demulsifying unwashed lysed cells comprising microbial oil to form an unwashed demulsified lysed cell composition; and then separating the oil from the unwashed demulsified lysed cell composition. An unwashed demulsified lysed cell composition refers to the process whereby the lysed cell composition is not washed, e.g., with water or buffer that is then removed by, e.g., centrifugation. Washing a lysed cell composition can decrease the overall yield of oil obtained from a cell.

In an alternative embodiment, the number of times the lysed cell composition is washed can be decreased by 1 time, 2 times, 3 times or more. In some embodiments, the washing is no more than 1 time, 2 times, or 3 times.

In some embodiments, the various combinations of forming a lysed cell composition, adding an emulsifier to the lysed cell composition, contacting a lysed cell composition with an acid or decreasing the pH of a lysed cell composition, contacting a lysed cell composition with a salt, heating the lysed cell composition, and agitating a lysed cell composition can occur in a single vessel. In some embodiments, the various combinations of forming cells, contacting cells with an acid or decreasing the pH of cells, adding an emulsifier to the lysed cell composition, contacting cells with a salt, heating the cells, and agitating cells can occur in a single vessel. In some embodiments, the single vessel includes a fermentation vessel. In some embodiments, the fermentation vessel can have a volume of at least 20,000 liters, at least 50,000 liters, at least 100,000 liters, at least 120,000 liters, at least 150,000 liters, at least 200,000 liters, or at least 220,000 liters. In some embodiments, the fermentation vessel can have a volume of 20,000 liters to 220,000 liters, 20,000 liters to 100,000 liters, 20,000 liters to 50,000 liters, 50,000 liters to 220,000 liters, 50,000 liters to 150,000 liters, 50,000 liters to 100,000 liters, 100,000 liters to 220,000 liters, 100,000 liters to 150,000 liters, 100,000 liters to 120,000 liters, 150,000 liters to 220,000 liters, 150,000 liters to 200,000 liters, or 200,000 liters to 220,000 liters.

In some embodiments, a quantity of cells and/or lysed cell composition formed in a vessel can be transferred into one or more agitation vessels. In some embodiments, the agitation vessels can have a volume of at least 20,000 liters, at least 30,000 liters, at least 40,000 liters or at least 50,000 liters. In some embodiments, the agitation vessels can have a volume of 20,000 liters to 50,000 liters, 20,000 liters to 40,000 liters, 20,000 liters to 30,000 liters, 30,000 liters to 50,000 liters, 30,000 liters to 40,000 liters or 40,000 liters to 50,000 liters.

In general, the processes described herein do not utilize an organic solvent to obtain, separate, or otherwise recover a microbial oil from the microbial cells. In some embodiments, no organic solvent is used in obtaining microbial oil from microbial cells. In another embodiment, an organic solvent is not added to cells, is not added to a lysed cell composition, and/or is not added to an oil during the processes disclosed herein in an amount or concentration sufficient to obtain a microbial oil. Organic solvents include polar solvents, non-polar solvents, water-miscible solvents, water-immiscible solvents, and combinations thereof.

In some embodiments, the process further comprises separating an oil from a demulsified lysed cell composition. In some embodiments, the process comprises separating an oil from the demulsified lysed cell composition by centrifuging the demulsified lysed cell composition. In some embodiments, an oil is separated from a demulsified lysed cell composition by allowing the demulsified lysed cell composition to stand, wherein the oil separates (e.g., as a separate layer) from the demulsified lysed cell composition using gravity. In some embodiments, separation is achieved by a lipophilic membrane. In some embodiments, the separating comprises centrifuging at a temperature of 10° C. to 100° C. In some embodiments, the oil is separated from the demulsified lysed cell composition by first raising the pH (e.g. by adding a base that is described hereinabove) and then centrifuging the demulsified lysed cell composition to obtain the oil.

In some embodiments, the pH of the demulsified lysed cell composition is raised by adding a base to the demulsified lysed cell composition. Bases that can be added to the demulsified lysed cell composition are the same as those set forth hereinabove. In some embodiments, the pH is selected from about 7.5 or above; about 8 or above; about 9 or above; about 10 or above; about 11 or above; and about 12 or above. In other embodiments, the pH is selected from a pH of 7 to 13; 7 to 12; 7 to 11; 7 to 10; 7 to 9; 8 to 13; 8 to 12; 8 to 11; 8 to 10; 8 to 9; 9 to 12; 9 to 11; 9 to 10; 10 to 12; and 10 to 11.

In some embodiments, the process comprises separating an oil from the demulsified lysed cell composition by centrifuging the demulsified lysed cell composition at a temperature of at least 10° C., at least 20° C., at least 25° C., at least 30° C., at least 35° C., at least 40° C., at least 45° C., at least 50° C., at least 55° C., at least 60° C., at least 65° C., at least 70° C., at least 75° C., at least 80° C., at least 85° C., at least 90° C., at least 95° C., or at least 100° C. In some embodiments, the process comprises separating an oil from the demulsified lysed cell composition by centrifuging the demulsified lysed cell composition at a temperature of 10° C. to 100° C., 10° C. to 90° C., 10° C. to 80° C., 20° C. to 100° C., 20° C. to 90° C., 20° C. to 80° C., 25° C. to 100° C., 25° C. to 90° C., 25° C. to 80° C., 25° C. to 75° C., 30° C. to 100° C., 30° C. to 90° C., 30° C. to 80° C., 40° C. to 100° C., 40° C. to 90° C., 40° C. to 80° C., 50° C. to 100° C., 50° C. to 90° C., 50° C. to 80° C., 50° C. to 70° C., 60° C. to 100° C., 60° C. to 90° C., 60° C. to 80° C., 60° C. to 70° C., 70° C. to 100° C., 70° C. to 90° C., 70° C. to 80° C., 80° C. to 100° C., 80° C. to 90° C., or 90° C. to 100° C.

In some embodiments, centrifuging is conducted at a feed rate (of a demulsified lysed cell composition into a centrifuge) of 1 kilogram per minute (kg/min) to 500 kg/min, 1 kg/min to 400 kg/min, 1 kg/min to 300 kg/min, 1 kg/min to 200 kg/min, 1 kg/min to 100 kg/min, 1 kg/min to 75 kg/min, 1 kg/min to 50 kg/min, 1 kg/min to 40 kg/min, 1 kg/min to 30 kg/min, 1 kg/min to 25 kg/min, 1 kg/min to 10 kg/min, 10 kg/min to 500 kg/min, 10 kg/min to 400 kg/min, 10 kg/min to 300 kg/min, 10 kg/min to 200 kg/min, 10 kg/min to 100 kg/min, 10 kg/min to 75 kg/min, 10 kg/min to 50 kg/min, 10 kg/min to 40 kg/min, 10 kg/min to 30 kg/min, 20 kg/min to 500 kg/min, 20 kg/min to 400 kg/min, 20 kg/min to 300 kg/min, 20 kg/min to 200 kg/min, 20 kg/min to 100 kg/min, 20 kg/min to 75 kg/min, 20 kg/min to 50 kg/min, 20 kg/min to 40 kg/min, 25 kg/min to 500 kg/min, 25 kg/min to 400 kg/min, 25 kg/min to 300 kg/min, 25 kg/min to 200 kg/min, 25 kg/min to 100 kg/min, 25 kg/min to 75 kg/min, 25 kg/min to 50 kg/min, 30 kg/min to 60 kg/min, 30 kg/min to 50 kg/min, 30 kg/min to 40 kg/min, 50 kg/min to 500 kg/min, 100 kg/min to 500 kg/min, or 200 kg/min to 500 kg/min.

In some embodiments, the process comprises centrifuging a demulsified lysed cell composition at a centrifugal force of 1,000 g to 25,000 g, 1,000 g to 20,000 g, 1,000 g to 10,000 g, 2,000 g to 25,000 g, 2,000 g to 20,000 g, 2,000 g to 15,000 g, 3,000 g to 25,000 g, 3,000 g to 20,000 g, 5,000 g to 25,000 g, 5,000 g to 20,000 g, 5,000 g to 15,000 g, 5,000 g to 10,000 g, 5,000 g to 8,000 g, 10,000 g to 25,000 g, 15,000 g to 25,000 g, or at least 1,000 g, at least 2,000, g, at least 4,000 g, at least 5,000 g, at least 7,000 g, at least 8,000 g, at least 10,000 g, at least 15,000 g, at least 20,000 g, or at least 25,000 g. As used herein, "g" refers to standard gravity or approximately 9.8 m/s². In some embodiments, the process comprises centrifuging a demulsified lysed cell composition at 4,000 rpm to 14,000 rpm, 4,000 rpm to 10,000 rpm, 6,000 rpm to 14,000 rpm, 6,000 rpm to 12,000 rpm, 8,000 to 14,000 rpm, 8,000 rpm to 12,000 rpm, or 8,000 rpm to 10,000 rpm.

In some embodiments, the oil can be recovered, for example, by decanting, skimming, vacuuming, pumping, sucking off, drawing off, siphoning, or otherwise recovering the microbial oil from the surface of the separated composition.

In some embodiments, the process comprises drying the oil that has been recovered to remove water from the oil. In some embodiments, drying the oil can include, but is not limited to, heating the oil to evaporate water. In some embodiments, after drying, the oil has a water content by weight (or volume) percentage of oil that is less than 3%, less than 2.5%, less than 2%, less than 1.5%, less than 1%, less than 0.5%, less than 0.1%, or 0%. In some embodiments, after drying, the oil has a water content by weight (or volume) percentage of oil of 0% to 3%, 0% to 2.5%, 0% to 2%, 0% to 1.5%, 0% to 1%, 0% to 0.5%, 0.1% to 3%, 0.1% to 2.5%, 0.1% to 2%, 0.1% to 1.5%, 0.1% to 1%, 0.1% to 0.5%, 0.5% to 3%, 0.5% to 2.5%, 0.5% to 2%, 0.5% to 1.5%, 0.5% to 1%, 1% to 3%, 1% to 2.5%, 1% to 2%, 1% to 1.5%, 1.5% to 3%, 1.5% to 2.5%, 1.5% to 2%, 2% to 3%, 2% to 2.5%, or 2.5% to 3%.

Disclosed herein is a microbial oil that can be obtained from microbial cells by any of the processes disclosed herein. In some embodiments, the oil comprises at least 30% by weight (or volume) arachidonic acid. In some embodiments, the oil comprises at least 30% by weight (or volume) docosahexaenoic acid.

The Anisidine value (AV) is determined in accordance with AOCS Official Method Cd 18-90. In one embodiment, the oil described herein has an AV of less than about 50; less than about 40; less than about 30; less than about 20; less than about 15; or less than about 10. In some embodiments, the oil has an AV of less than about 50. The term anisidine value refers to the measure of secondary reaction products, such as aldehydes and ketones that occur during oxidation of the oil.

The peroxide value (PV) is determined in accordance with the AOCS Official Method Cd 8-53. In one embodiment, the oil described herein has a PV less than about 20 meq/kg; less than about 10 meq/kg; or less than about 5 meq/kg. In some embodiments, the oil has a PV of less than about 5 meq/kg. The term peroxide value refers to the measure of primary reaction products, such as peroxides and hydroperoxides, that occur during oxidation of the oil. As used herein peroxide value is measured in meq/kg.

In some embodiments, the oil has a phosphorus content of 100 ppm or less, 95 ppm or less, 90 ppm or less, 85 ppm or less, 80 ppm or less, 75 ppm or less, 70 ppm or less, 65 ppm or less, 60 ppm or less, 55 ppm or less, 50 ppm or less, 45 ppm or less, 40 ppm or less, 35 ppm or less, 30 ppm or less, 25 ppm or less, 20 ppm or less, 15 ppm or less, 10 ppm or less, 9 ppm or less, 8 ppm or less, 7 ppm or less, 6 ppm or less, 5 ppm or less, 4 ppm or less, 3 ppm or less, 2 ppm or less, or 1 ppm or less. In some embodiments, the oil has a phosphorus content of about 8 ppm or less.

In some embodiments, the oil comprises one or more PUFAs. In some embodiments, the oil comprises at least 10%, at least 15%, at least 20%, at least 25%, at least 30%, at least 35%, at least 40%, at least 45%, at least 50%, at least 60%, at least 70% or at least 80% PUFA (by PUFA weight). In some embodiments, the oil comprises at least 10%, at least 15%, at least 20%, at least 25%, at least 30%, at least 35%, at least 40%, at least 45%, at least 50%, at least 60%, at least 70% or at least 80% DHA (by DHA weight), and/or at least 10%, at least 15%, or at least 20% DPA n-6 (by DPA n-6 weight), and/or at least 10%, at least 15%, or at least 20% EPA (by EPA weight), and/or at least 10%, at least 15%, at least 20%, at least 25%, at least 30%, at least 35%, at least 40%, at least 45%, at least 50%, at least 55%, at least 60%, at least 65%, at least 70%, at least 75%, or at least 80% ARA (by ARA weight). In some embodiments, an oil comprises less than 50%, less than 40%, less than 30%, less than 20%, less than 15%, less than 10%, or less than 5% EPA (by EPA weight). In some embodiments, an oil comprises less than 50%, less than 40%, less than 30%, less than 20%, less than 15%, less than 10%, or less than 5% DHA (by DHA weight). In some embodiments, an oil comprises less than 10%, less than 5%, less than 2%, less than 1%, or less than 0.5% by weight (or volume) sterols.

In some embodiments, an oil comprises at least 50%, at least 60%, at least 70%, at least 80%, at least 90%, at least 95%, or 50% to 95%, 50% to 90%, 50% to 85%, 50% to 80%, 50% to 75%, 60% to 95%, 60% to 90%, 60% to 85%, 70% to 95%, 70% to 90%, 70% to 85%, 75% to 95%, 75% to 90%, or 75% to 85%, by weight (or volume) of triglycerides.

In some embodiments, the triglycerides comprise at least 10%, at least 20%, at least 30%, at least 35%, at least 40%, at least 50%, at least 60%, at least 70% or at least 80% by weight (or volume) DHA. In some embodiments, the triglycerides comprise at least 10%, at least 20%, at least 30%, at least 35%, at least 40%, at least 45%, at least 50%, at least 55%, at least 60%, at least 65%, at least 70%, at least 75%, or at least 80% by weight (or volume) ARA. In some embodiments, the triglycerides comprise at least 50%, at least 40%, at least 30%, at least 20%, at least 15%, at least 10%, or at least 5% by weight (or volume) EPA.

In one embodiment, the microbial oil obtained and/or recovered by any of the processes described herein is a crude oil. In another embodiment, the oil described herein is a refined oil. A "crude oil" is an oil obtained from microbial cells without further processing. A "refined oil" is an oil obtained by treating a crude oil with standard processing of refining, bleaching, and/or deodorizing. See, e.g., U.S. Pat. No. 5,130,242. In some embodiments, refining includes, but is not limited to, caustic refining, degumming, acid treatment, alkali treatment, cooling, heating, bleaching, deodorizing, deacidification, and combinations thereof.

In some embodiments, the process comprises concentrating a fermentation broth comprising microbial cells. In some embodiments, the process comprises concentrating the lysed cell composition. As used herein, "concentrating" refers to removing water from a composition. Concentrating can include, but is not limited to, evaporating, chemical drying, centrifuging, and the like, and combinations thereof. In some embodiments, a cell composition or a lysed cell composition is concentrated to provide an oil concentration of at least 4%, at least 5%, at least 10%, at least 15%, at least 20%, at least 25%, or at least 30% by weight (or volume) of the lysed cell composition. In some embodiments, a cell composition or a lysed cell composition is concentrated to provide an oil concentration of 4% to 40%, 4% to 30%, 4% to 20%, 4% to 15%, 5% to 40%, 5% to 30%, 5% to 20%, 10% to 40%, 10% to 30%, 10% to 20%, 15% to 40%, 15% to 30%, 20% to 40%, 20% to 30%, 25% to 40%, or 30% to 40% by weight (or volume) of the lysed cell composition.

Effective culture conditions for a microbial cell for use with the invention include, but are not limited to, effective media, bioreactor, temperature, pH, and oxygen conditions that permit oil production. An effective medium refers to any medium in which a microbial cell, e.g., Thraustochytriales microbial cell, is typically cultured. Such media typically comprises an aqueous medium having assimilable carbon, nitrogen, and phosphate sources, as well as appropriate salts, minerals, metals, and other nutrients, such as vitamins. Microbial cells for use with the present invention can be cultured in conventional fermentation bioreactors, shake flasks, test tubes, microtiter dishes, and petri plates.

In some embodiments, a microbial cell comprises at least 30% by weight (or volume) oil, at least 35% by weight (or volume) oil, at least 40% by weight (or volume) oil, at least 50% by weight (or volume) oil, at least 60% by weight (or volume) oil, at least 70% by weight (or volume) oil, or at least 80% by weight (or volume) oil. In some embodiments, a microbial cell for use with the present invention is capable of producing at least 0.1 grams per liter per hour (g/L/h) of DHA, at least 0.2 g/L/h of DHA, at least 0.3 g/L/h of DHA, or at least 0.4 g/L/h of DHA. In some embodiments, a microbial cell for use with the present invention is capable of producing at least 0.01 grams per liter per hour (g/L/h) of ARA, at least 0.05 g/L/h of ARA, at least 0.1 g/L/h of ARA, at least 0.2 g/L/h of ARA, at least 0.3 g/L/h of ARA, or at least 0.4 g/L/h of ARA.

In some embodiments, an oil obtained according to any of the processes described herein, the spent biomass, or combinations thereof can be used directly as a food or food ingredient, such as an ingredient in baby food, infant formula, beverages, sauces, dairy based foods (such as milk, yogurt, cheese and ice-cream), oils (e.g., cooking oils or salad dressings), and baked goods; nutritional supplements (e.g., in capsule or tablet forms); feed or feed supplement for any non-human animal (e.g., those whose products (e.g., meat, milk, or eggs) are consumed by humans); food supplements; and pharmaceuticals (in direct or adjunct therapy application). The term "animal" refers to any organism belonging to the kingdom Animalia and includes any human animal, and non-human animal from which products (e.g., milk, eggs, poultry meat, beef, pork or lamb) are derived. In some embodiments, the oil and/or biomass can be used in seafood. Seafood is derived from, without limitation, fish, shrimp and shellfish. The term "products" includes any product derived from such animals, including, without limitation, meat, eggs, milk or other products. When the oil and/or biomass is fed to such animals, polyunsaturated oils can be incorporated into the flesh, milk, eggs or other products of such animals to increase their content of these oils.

EXAMPLES

Example 1

A cell broth (300 g) containing microbial cells (*Schizochytrium* sp.) was pasteurized at 60° C. for 1 hour. The unwashed cell broth was agitated at a speed of 180 RPM and heated to 60° C. The cells were lysed by adding a 50 wt % NaOH solution to pH adjust the broth to 7-7.5 and Alcalase® 2.4 FG (available from Novozymes (Franklinton, N.C.)) in an amount of 0.5% based on broth weight. While maintaining the agitation, the pH of the lysed cell composition was adjusted to 4 by adding a 98% $H_2SO_4$ by weight solution. Solid NaCl in an amount of 2% by weight of the lysed cell composition was added and the composition heated to 90° C. and held for 20 hours. The pH of the composition was adjusted to 7.5-8.5 by adding a 50 wt % NaOH solution and then centrifuged (Thermo Scientific Sorvell ST40R Centrifuge) at 8000 RPM for 5 minutes to provide a crude oil, which yielded 91.7% DHA (by weight DHA).

Example 2

A cell broth (300 g) containing microbial cells (*Schizochytrium* sp.) was pasteurized at 60° C. for 1 hour. A demulsified lysed cell composition was formed by adding a 20% $H_2SO_4$ by weight solution to adjust the pH of the cell broth to 2 and then heating the broth to 90° C. and holding for 45 hours. The microbial oil was separated from the demulsified lysed cell composition by adding a 50 wt % NaOH solution to adjust the pH of the composition to 7.5-8.5 and then centrifuging (Thermo Scientific Sorvell ST40R Centrifuge) the composition at 8000 RPM for 5 minutes to provide a crude oil, which yielded 51.62% DHA (by DHA weight).

Example 3

A cell broth (300 g) containing microbial cells (*Schizochytrium* sp.) was pasteurized at 60° C. for 1 hour. A demulsified lysed cell composition was formed by adding: a 20% $H_2SO_4$ by weight solution to adjust the pH of the cell broth to 2, solid NaCl in an amount of 2% by weight of the broth; and heating the broth 90° C. and holding for 18 hours. The microbial oil was separated from the demulsified lysed cell composition by centrifuging (Thermo Scientific Sorvell ST40R Centrifuge) the composition at 8000 RPM for 5 minutes to provide a crude oil, which yielded 38.82% DHA (by DHA weight).

Example 4

A cell broth (300 g) containing microbial cells (*Schizochytrium* sp.) was pasteurized at 60° C. for 1 hour. A demulsified lysed cell composition was formed by adding 2%, by weight broth, of a 98% $H_2SO_4$ by weight solution and heating the broth to 90° C. for 4 hour. The microbial oil was separated from the demulsified lysed cell composition by adding a 50 wt % NaOH solution to adjust the pH of the composition to 7-8.5, holding for 21 hours at 90° C., and centrifuging (Thermo Scientific Sorvell ST40R Centrifuge)

the composition at 8000 RPM for 5 minutes to provide a crude oil, which yielded 72% DHA (by weight DHA).

The crude oil had an Anisidine Value (AV) of 14.5.

Example 5

A cell broth (300 g) containing microbial cells (*Schizochytrium* sp.) was pasteurized at 60° C. for 1 hour. The unwashed cell broth was agitated at a speed of 180 RPM and heated to 60° C. The cells were lysed by adding: 50 wt % NaOH to pH adjust the broth to 7-7.5, and Alcalase 2.4 FG (available from Novozymes (Franklinton, N.C.) in an amount of 0.5% based on broth weight. While maintaining the agitation, the pH of the lysed cell composition was adjusted to 4 by adding a 98% $H_2SO_4$ by weight solution, and then heating the composition to 90° C. After 45 hours at 90° C., the composition was centrifuged (Thermo Scientific Sorvell ST40R Centrifuge) at 8000 RPM for 5 minutes to provide a crude oil, which yielded 81% DHA (by DHA weight). The crude oil has an AV of 14.5.

Example 6

A cell broth (300 g) containing microbial cells (*Schizochytrium* sp.) was pasteurized at 60° C. for 1 hour. A demulsified lysed cell composition was formed by adding 2.5%, by weight broth, of a 98% $H_2SO_4$ by weight solution, and then heating the broth to 90° C. for 5 hours. The microbial oil was separated from the demulsified lysed cell composition by adding a 50 wt % NaOH solution to adjust the pH of the composition to 7-8.5 and, after a few hours at 90° C., centrifuging (Thermo Scientific Sorvell ST40R Centrifuge) the composition at 8000 RPM for 5 minutes to provide a crude oil, which yielded 92.5% DHA (by DHA weight).

Example 7

A cell broth (350 g) containing microbial cells (*Schizochytrium* sp.) was pasteurized at 60° C. for 1 hour. A demulsified lysed cell composition was formed by adding 2%, by weight broth, of a 98% $H_2SO_4$ by weight solution, and then heating the broth to 90° C. for 5-6 hours. The microbial oil was separated from the demulsified lysed cell composition by adding a 50 wt % NaOH solution to adjust the pH to 7-8.5 and, after a few hours at 90° C., centrifuging (Thermo Scientific Sorvell ST40R Centrifuge) the composition at 8000 RPM for 5 minutes to provide a crude oil, which yielded 82.63% DHA (by DHA weight).

Example 8

A cell broth (350 g) containing microbial cells (*Schizochytrium* sp.) was pasteurized at 60° C. for 1 hour. A demulsified lysed cell composition was formed by adding 1%, by weight broth, of a 98% $H_2SO_4$ by weight solution, and heating the broth to 90° C. for 5-10 hours. The microbial oil was separated from the demulsified lysed cell composition by adding a 50 wt % NaOH solution to adjust the pH to 7-8.5 and centrifuging (Thermo Scientific Sorvell ST40R Centrifuge) the composition at 8000 RPM for 5 minutes to provide a crude oil, which yielded 42% DHA (by DHA weight).

Example 9

A cell broth (350 g) containing microbial cells (*Schizochytrium* sp.) was pasteurized at 60° C. for 1 hour. A demulsified lysed cell composition was formed by adding 3%, by weight broth, of a 98% $H_2SO_4$ by weight solution and heating the broth to 90° C. for 1-5 hours. The microbial oil was separated from the demulsified lysed cell composition by adding a 50 wt % NaOH solution to adjust the pH to 7-8.5 and centrifuging (Thermo Scientific Sorvell ST40R Centrifuge) the composition at 8000 RPM for 5 minutes to provide a crude oil, which yielded 88% DHA (by DHA weight).

Example 10

A cell broth (350 g) containing microbial cells (*Schizochytrium* sp.) was pasteurized at 60° C. for 1 hour. A demulsified lysed cell composition was formed by adding 4%, by weight broth, of a 70 wt % nitric acid solution and heating the broth to 90° C. for 1 hour. The microbial oil was separated from the demulsified lysed cell composition by adding a 50 wt % NaOH solution to adjust the pH to 7-8.5 and centrifuging (Thermo Scientific Sorvell ST40R Centrifuge) the composition at 8000 RPM for 5 minutes to provide a crude oil, which yielded 82% DHA (by DHA weight).

Example 11

A cell broth (350 g) containing microbial cells (*Schizochytrium* sp.) was pasteurized at 60° C. for 1 hour. A demulsified lysed cell composition was formed by adding 2%, by weight broth, of a 70 wt % nitric acid solution and heating the broth to 90° C. for 5-6 hours. The microbial oil was separated from the demulsified lysed cell composition by adding a 50 wt % NaOH solution to adjust the pH to 7-8.5 and centrifuging (Thermo Scientific Sorvell ST40R Centrifuge) the composition at 8000 RPM for 5 minutes to provide a crude oil, which yielded 58.5% DHA (by DHA weight).

Example 12

A cell broth (350 g) containing microbial cells (*Schizochytrium* sp.) was pasteurized at 60° C. for 1 hour. A demulsified lysed cell composition was formed by adding 2.5%, by weight broth, of a 70% nitric acid solution and heating the broth to 90° C. for 5 hours. The microbial oil was separated from the demulsified lysed cell composition by adding a 50 wt % NaOH solution to adjust the pH to 7-8.5 and, after a few hours at 90° C., centrifuging (Thermo Scientific Sorvell ST40R Centrifuge) the composition at 8000 RPM for 5 minutes to provide a crude oil, which yielded 74% DHA (by DHA weight).

Example 13

A cell broth (350 g) containing microbial cells (*Schizochytrium* sp.) was pasteurized at 60° C. for 1 hour. A demulsified lysed cell composition was formed by adding 4%, by weight broth, of phosphoric acid and heating the broth to 90° C. for 5 hours. The microbial oil was separated from the demulsified lysed cell composition by adding a 50 wt % NaOH solution to adjust the pH to 7-8.5 and, after a few hours at 90° C., centrifuging (Thermo Scientific Sorvell ST40R Centrifuge) the composition at 8000 RPM for 5 minutes to recover the crude oil. A 45 g sample of this composition yielded 1.0 mL of crude oil.

Example 14

A cell broth (350 g) containing microbial cells (*Schizochytrium* sp.) was pasteurized at 60° C. for 1 hour. A demulsified lysed cell composition was formed by adding 8%, by weight broth, of phosphoric acid and heating the broth to 90° C. for 3 hours. The microbial oil was separated from the demulsified lysed cell composition by adding a 50 wt % NaOH solution to adjust the pH to 7-8.5 and, after a few hours at 90° C., centrifuging (Thermo Scientific Sorvell ST40R Centrifuge) the composition at 8000 RPM for 5 minutes to recover the crude oil. A 45 g sample of this composition yielded 0.5 mL of crude oil.

Example 15

A cell broth (2000 L) containing microbial cells (*Schizochytrium* sp.) was placed in a treatment tank agitating at 190 rpm. A demulsified lysed cell composition was formed by adding 4%, by weight broth, of a 98% $H_2SO_4$ by weight solution and heating the broth to 90-95° C. for 1 hour. The microbial oil was separated from the demulsified lysed cell composition by cooling the composition to 75° C., adding a 50 wt % NaOH solution to adjust the pH to 7-8.5, mixing the composition overnight, and centrifuging the composition in line at 1754 RPM at 8 L/min to provide a crude oil, which yielded 93% DHA (by DHA weight) and a crude oil with a Peroxide Value (PV) of 0.69 meq, an AV of 23.9, and a free fatty acid (FFA) content of 1.04.

Example 16

A cell broth (550 L) containing microbial cells (*Schizochytrium* sp.) was placed in a treatment tank agitating at 193 rpm. The cell broth was heated to 60° C., the pH adjusted to 7.3-7.5 by adding a 50 wt. % NaOH solution, and alcalase was added in an amount of 0.5% by weight broth. After 2 hours, the pH of the lysed cell composition was adjusted to 4 by adding a 98% $H_2SO_4$ by weight solution, and heated to 90° C. while maintaining the agitation. After 20 hours at 90° C., the microbial oil was separated from the demulsified lysed cell composition by cooling the composition to 75° C., adjusting the pH to 8.5 by adding a 50 wt. % NaOH solution, holding the composition overnight, and centrifuging the composition in line at 1754 RPM at 8 L/min to provide a crude oil, which yielded 84% DHA (by DHA weight) and a crude oil with a PV of 0 meq, an AV of 7.3, and a FFA content of 0.17.

Example 17

A cell broth (2500-3000 Liters) containing microbial cells (*Mortierella*) was placed in a decanting tank for several hours to settle. Once settled, 50-60% of the biomass free liquid was pumped off for discard. The concentrated unwashed pasteurized cell broth was then passed through a high shear mixer (Siemens ULTRA-Turrax UTL 1000/10 at 60 Hz) that was in line to the treatment tank. A demulsified lysed cell composition was formed by adding 3%, by weight broth, of a 98% $H_2SO_4$ by weight solution to adjust the pH to 0.9 to 1.5 and the broth heated to 94° C. for 20-24 hours or until a 1 mL in a 10 mL dilution of broth in deionized water yields a particle size of 25 μm or less. The demulsified lysed cell composition was diluted with deoxygenated water to a solids content of 10% (number generated using Omnimark Uwave moisture analyzer) and reheated to 85° C. if the water addition caused the temperature to drop below 85° C. The microbial oil was separated from the demulsified lysed cell composition by adding a 50% NaOH solution to adjust the pH to 7.8-8.2, allowing the composition to mix for 30 minutes or until centrifugation of a sample showed a complete absence of an emulsion layer, and centrifuging (Seital SR1010) the composition in line at 1750 RPM and at a flow rate of 7 liters/min for 7-10 hours to recover the crude oil.

Three separate batches of cell broth were each independently subjected to the above process.

The Batch 1 crude oil yielded 86.6% ARA (by ARA weight) and a dried, filtered crude oil with an AV of 26.1 and a PV of 0.39 meq.

The Batch 2 crude oil yielded 87.6% ARA (by ARA weight) and a dried, filtered crude oil with an AV of 14 and a PV of 0.31meq.

The Batch 3 crude oil yielded 85% ARA (by ARA weight) and a dried filtered crude oil with an AV of 24.7 and a PV of 0.51 meq.

Example 18

A cell broth (1000 mL) containing microbial cells (*Mortierella*) was pasteurized at 70° C. for 1 hour. A demulsified lysed cell composition was formed by adding 4%, by weight broth, nitric acid (70% solution) to adjust the pH to 0.7-1.0 and heating the broth to 90° C. while agitating at a speed of 200 rpm for 30 hours. The microbial oil was separated from the demulsified lysed cell composition by adding 50% w/w solution of NaOH to adjust the pH 8.0-8.2 and centrifuging (Thermo Sorvall ST 40R) the composition at 8,000 g for 5 minutes to provide a crude oil, which yielded 74.13% ARA (by ARA weight) and a crude oil with an AV of 27.9.

Example 19

A cell broth (1000 mL) containing microbial cells (*Mortierella*) was pasteurized at 70° C. for 1 hour. A demulsified lysed cell composition was formed by adding 15%, by weight broth, phosphoric acid (85% solution) to adjust the pH to 0.7 to 1.5 and heating the composition to 90° C. while agitating at a speed of 200 rpm for 50 hours. The microbial oil was separated from the demulsified lysed cell composition by adding 50% w/w solution of NaOH to adjust the pH 8.0-8.2 and centrifuging (Thermo Sorvall ST 40R) the composition at 8,000 g for 5 minutes to provide a crude oil, which yielded 42.61% ARA (by ARA weight). The crude oil had an AV of 16.1.

Example 20

A cell broth (1000 mL) containing microbial cells (*Mortierella*) was pasteurized at 70° C. for 1 hour. A demulsified lysed cell composition was formed by adding 6%, by weight broth, hydrochloric acid (32% solution) to adjust the pH to 0.7-1.5 and heating the broth to 90° C. while agitating at a speed of 200 rpm for 50 hours. The microbial oil was separated from the demulsified lysed cell composition by adding 50% w/w solution of NaOH to adjust the pH of the composition to 8.0-8.2 and centrifuging (Thermo Sorvall ST 40R) the composition at 8,000 g for 5 minutes to provide a crude oil, which yielded 72.61% ARA (by ARA weight). The crude oil had an AV of 11.1.

Example 21

A cell broth (300 g) containing microbial cells (*Schizochytrium* sp.) was pasteurized at 60° C. for 1 hour. A demulsified lysed cell composition was formed by: adding a 12.5 wt % NaOH solution to the cell broth to adjust the pH to 11, adding 2% NaCl, by weight broth, and heating the composition to 90° C. After 25 hours at 90° C., the microbial oil was separated from the demulsified lysed cell composition by centrifuging (Thermo Scientific Sorvell ST40R Centrifuge) the composition at 8000 RPM for 5 minutes to provide crude oil, which yielded 71% DHA (by DHA weight).

Example 22

An unwashed cell broth (2129.8 kg) containing microbial cells (*Mortierella*) was pasteurized at 70° C. for 1 hour and then passed through a high shear mixer (Siemens ULTRA-Turrax UTL 1000/10 at 60 Hz) that was in line to the treatment tank. A demulsified lysed cell composition was formed by: adding 3.5%, by weight broth, of a 98% sulfuric acid solution to adjust the pH to 0.07 to 1.5; heating to 90° C.; and holding for 28 hours while agitating at a speed of 200 RPM. The microbial oil was separated from the demulsified lysed cell composition by neutralizing the composition and adjusting the pH to 8.0 by addition of 50% NaOH and 2%, by weight composition, NaCl, and then centrifuging (Seital SR1010) the composition to provide a crude oil, which yielded 77.4% ARA (by ARA Weight) and a crude oil with an AV of 12.4, a FFA content of 2.27%, and a PV of 0.13 meq.

Example 23

A washed cell broth (750 g) containing microbial cells (*Crypthecodinium cohnii*) was pasteurized at 60° C. for 1 hour. The cells were mechanically lysed by passing the cell broth through a homogenizer (Microfluidizer M110) twice at 12,000 PSI. The lysed cell composition was placed in a round flask and demulsified by adding a 4%, by weight composition, sulfuric acid (98% pure) solution, heating to 90° C. while agitating at 200 RPM, and holding for 28 hours. The microbial oil was separated from the demulsified lysed cell composition by neutralizing the composition and adjusting the pH to 8.0 by addition of a 50% NaOH solution, and then centrifuging (Thermo Sorvall ST 40R) the composition at 8000 g for 5 minutes to provide a crude oil, which yielded 45% DHA (by DHA weight)(based on FAME analysis) and a crude oil with an AV of 12.35 and a PV of 1.09 meq.

Example 24

An unwashed cell broth (750 g) containing microbial cells (*Schizochytrium* sp.) was pasteurized at 60° C. for 1 hour and placed in a 1 L flask agitating at 250 RPM. The temperature was raised to 60° C. to decrease mix time due to viscosity. A demulsified lysed cell composition was formed by: adding 4%, by weight broth, of a 50% NaOH to adjust the pH to 12.62; heating to 90° C.; and allowing to react for 26 hours until the pH dropped to 7.75. The microbial oil was separated from the demulsified lysed cell composition by centrifuging (Thermo Sorvall ST 40R) the composition at 8000 g for 5 minutes to provide a crude oil, which yielded 88% DHA (by DHA weight) (based on FAME analysis).

Example 25

An unwashed cell broth (750 g) containing microbial cells (*Schizochytrium* sp.) was pasteurized at 60° C. for 1 hour and placed in a 1 L flask agitating at 250 RPM. The temperature was raised to 60° C. to decrease mix time due to viscosity. A demulsified lysed cell composition was formed by: adding 4%, by weight broth, of a 50% NaOH solution to adjust the pH to 12.93; heating to 90° C.; and allowing to react for 26 hours until the pH dropped to 7.95. The microbial oil was separated from the demulsified lysed cell composition by centrifuging (Thermo Sorvall ST) the composition at 8000 g for 5 minutes to provide a crude oil, which yielded 82.5% DHA (by DHA weight) (based on FAME analysis).

Example 26

An unwashed cell broth (750 g) containing microbial cells (*Schizochytrium* sp.) was pasteurized at 60° C. for 1 hour and placed in a 1 L flask agitating at 250 RPM. The temperature was raised to 60° C. to decrease mix time due to viscosity and the pH raised to 7.5. A demulsified lysed cell composition was formed by: adding 3.5%%, by weight broth, of a 50% NaOH solution to adjust the pH to 12.28; heating to 90° C.; and allowing to react for 32 hours until the pH dropped to 7.88. The microbial oil was separated from the demulsified lysed cell composition by centrifuging (Thermo Sorvall ST 40R) the composition at 8000 g for 5 minutes to provide a crude oil, which yielded 88% DHA (by DHA weight) (based on FAME Analysis).

Example 27

An unwashed cell broth (750 g) containing microbial cells (*Schizochytrium* sp.) was pasteurized at 60° C. for 1 hour and placed in a 1 L flask agitating at 250 RPM. The temperature was raised to 60° C. to decrease mix time due to viscosity. A demulsified lysed cell composition was formed by: adding 4.0%, by weight broth, of a 50% NaOH solution to adjust to a pH of 12.87; heating to 90° C.; and allowing to react for 36 hours until the pH dropped to 8.15. The microbial oil was separated from the demulsified lysed cell composition by centrifuging (Thermo Sorvall ST 40R) the composition at 8000 g for 5 minutes to provide a crude oil, which yielded 84% DHA (by DHA weight) (based on FAME analysis).

Comparative Example 1

Cell broth (300 g) containing microbial cells (*Schizochytrium* sp.) was pasteurized at 60° C. for 1 hour. The unwashed cell broth was agitated at a speed of 180 RPM and heated to 60° C. The cells were lysed by adding 50 wt % NaOH solution to pH adjust the cells to 7-7.5 and Alcalase® 2.4 FG (available from, Novazymes (Franklinton, N.C.)) in an amount of 0.5% based on broth weight. While maintaining the agitation, the lysed cell composition was demulsified by simultaneously adding 12.5 wt % NaOH solution to adjust the pH to 10-11 and $CaCl_2$ in an amount of 2%, by weight composition, and then heating the composition to 90° C. and holding for 68 hours. The microbial oil was separated from the demulsified lysed cell composition by centrifuging (Thermo Scientific Sorvell ST40R Centrifuge) the composition at 8000 RPM for 5 minutes to provide crude oil, which yielded 62.5% DHA (by DHA weight) and a crude oil with an AV of 43.8.

What is claimed is:
1. A process for obtaining a microbial oil comprising one or more polyunsaturated fatty acids from one or more microbial cells, wherein the process comprises:
   (a) lysing the cells comprising the microbial oil to form a lysed cell composition;
   (b) demulsifying the lysed cell composition by adding an acid to form a demulsified lysed cell composition;

(c) separating the oil from the demulsified lysed cell composition; and
(d) recovering the oil;
wherein (b) comprises lowering the pH of the lysed cell composition to a pH of from about 0.5 to 6.0.

2. The process of claim 1, wherein at least one of (a) or (b) further comprises heating the cells or the composition to at least 70° C.

3. The process of claim 2, wherein at least one of (a) or (b) further comprises heating the cells or the composition to from about 70° C. to about 100° C.

4. The process of claim 1, wherein (b) further comprises adding an emulsifier to the lysed cell composition.

5. The process of claim 1, wherein (b) further comprises adding an acid in an amount of from about 0.5% to about 20%, by weight, lysed cell composition.

6. The process of claim 1, wherein (b) further comprises adding a salt in an amount of from about 0.05% to about 20%, by weight, of the lysed cell composition.

7. The process of claim 1, wherein (b) further comprises agitating the lysed cell composition.

8. The process of claim 1, wherein (a) further comprises agitating the cells.

9. The process according to claim 1, wherein the acid is selected from sulfuric, phosphoric, hydrochloric, hydrobromic, hydroiodic, hypochlorous, chlorous, chloric, perchloric, fluorosulfuric nitric, fluoroantimonic, fluoroboric, hexafluorophosphoric, chromic, boric, acetic, citric, formic, and combinations thereof.

10. The process of claim 9, wherein the acid is sulfuric.

11. The process of claim 1, wherein the cells of (a) are unwashed.

12. The process of claim 1, wherein the cells of (a) are contained in a fermentation broth.

13. The process of claim 1, wherein (c) further comprises centrifuging the demulsified lysed cell composition.

14. The process of claim 1, wherein the polyunsaturated fatty acid is selected from an omega-3 fatty acid, an omega-6 fatty acid, and mixtures thereof.

15. The process of claim 1, wherein the polyunsaturated fatty acid is selected from docosahexaenoic acid (DHA), eicosapentaenoic acid (EPA), docosapentaenoic acid (DPA), arachidonic acid (ARA), gamma-linolenic acid (GLA), dihomo-gamma-linolenic acid (DGLA), stearidonic acid (SDA), and mixtures thereof.

16. The process of claim 15, wherein the polyunsaturated fatty acid is docosahexaenoic acid (DHA).

17. The process of claim 15, wherein the polyunsaturated fatty acid is arachidonic acid (ARA).

18. The process of claim 1, wherein the microbial cells are algae, yeast, fungi, protist, or bacteria cells.

19. The process of claim 1, wherein the microbial cells are from the genus *Mortierella*, genus *Crypthecodinium*, or order Thraustochytriales.

20. The process of claim 18, wherein the microbial cells are from the order Thraustochytriales.

21. The process of claim 19, wherein the microbial cells are from the genus *Thraustochytrium, Schizochytrium,* or mixtures thereof.

22. The process of claim 18, wherein the microbial cells are from *Mortierella* Alpine.

23. The process of claim 1, wherein the lysed cell composition comprises liquid, cell debris, and microbial oil.

24. The process of claim 1, wherein an organic solvent is not used to obtain the oil from the cells.

25. The process of claim 1, wherein the mean particle size of the demulsified lysed cell composition is 25 microns or less.

26. The process of claim 4, wherein the emulsifier is an ionic emulsifier.

27. The process of claim 26, wherein the ionic emulsifier is an anionic emulsifier selected from an anionic sulfate emulsifier, an anionic sulfonate emulsifier, an anionic phosphate emulsifier, an anionic carboxylate emulsifier, and combinations thereof.

28. The process of claim 27, wherein the ionic emulsifier is an anionic sulfate emulsifier selected from ammonium lauryl sulfate, sodium dodecyl sulfate, sodium laureth sulfate, sodium lauryl ether sulfate, sodium myreth sulfate, and combinations thereof.

29. The process of claim 4, wherein the emulsifier is added in an amount of from 0.2% to 10% by weight of the lysed cell composition.

30. The process of claim 6, wherein the salt is selected from the group consisting of alkali metal salts, alkali earth metal salts, sulfate salts, and combinations thereof.

31. The process of claim 1, wherein the oil of (d) is a crude oil.

32. The process of claim 31, wherein (d) further comprises refining the crude oil to obtain a refined oil.

33. The process of claim 1, wherein the oil comprises at least 30% by weight arachidonic acid.

34. The process of claim 1, wherein the oil comprises at least 30% by weight docosahexaenoic acid.

35. The process of claim 1, wherein the oil has an anisidine value of less than about 50.

36. The process of claim 1, wherein the oil has a phosphorus content of about 8 ppm or less.

37. The process of claim 1, wherein the oil has a peroxide value of less than about 5 meq/kg.

38. The process according to claim 1 wherein (a) and (b) are combined together to form a one-step lysing and demulsifying step.

39. The process according to claim 1, wherein (c) further comprises raising the pH of the demulsified lysed cell composition.

40. A process for obtaining a microbial oil comprising one or more polyunsaturated fatty acids from one or more microbial cells, wherein the process comprises:
(a) lysing the cells comprising the microbial oil by adding an acid to form a demulsified lysed cell composition having a pH from about 0.5 to 6;
(b) separating the oil from the demulsified lysed cell composition; and
(c) recovering the oil;
wherein said demulsified lysed cell composition is obtained during said lysing.

* * * * *